United States Patent [19]

Mathur et al.

[11] Patent Number: 5,700,672
[45] Date of Patent: Dec. 23, 1997

[54] PURIFIED THERMOSTABLE PYROCOCCUS FURIOUSUS DNA LIGASE

[75] Inventors: Eric J. Mathur, Carlsbad; Edward J. Marsh, Del Mar; Warren E. Schoettlin, San Diego, all of Calif.

[73] Assignee: Stratagene, La Jolla, Calif.

[21] Appl. No.: 919,140

[22] Filed: Jul. 23, 1992

[51] Int. Cl.$^6$ .............................. C12N 9/00; C12N 15/52
[52] U.S. Cl. .................... 435/183; 536/23.2; 435/69.1; 435/71.2
[58] Field of Search ................... 536/27, 23.2; 435/183, 435/69.1, 71.2

[56] References Cited

FOREIGN PATENT DOCUMENTS 0117239  11/1991  WIPO.

OTHER PUBLICATIONS

Barany, F., et al., "Cloning, overexpression and nucleotide sequence of a thermostable DNA ligase–encoding gene," Gene 109:1–11 (1991).
Barany, F., "The ligase chain reaction in a PCR world." PCR Methods and Applications, 1:5–16 (1991).
Barany, F., "Genetic disease detection and DNA amplification using cloned thermostable DNA ligase," P.N.A.S. 88:189–193 (1990).
Bond., S., "New methods for detecting HPV," 425–434. 1990.
Bryant, F. et al., "Characterization of hydrogenase from the hyperthermophilic Archeabacterium, Pyrococcus furiosus," J. Biol. Chem. 264:5070–5079 (1989).
Fiala, G. et al., "Pyrococcus furiosus sp. nov. represents a novel genus of marine heterotrophic archaebacteria growing optimally at 100°C" Arch. Microbiol. 145:56–61 (1986).
Landegren, U., et al., "DNA diagnostics—molecular techniques and automation." Science 241:1077–1080 (1988.
Landegren, U., et al., "A Ligase–mediated gene detection technique." Science 242:229–237 (1988).
Marsh, E., et al., "Pyrococcus furiosus DNA ligase and the ligase chain reaction." Strategies 5:73–76 (1992).
Pledger, R., et al., "Preliminary description and nutritional characterization of a chemoorganotrophic archaeobacterium growing at temperatures of up to 110°C. isolated from a submarine hydrothermal vent environment." J. General Microbiol. 137:203–211 (1991).

Takahashi, M., et al., "Thermophilic DNA ligase. Purification and properties of the enzyme from Thermus thermophilus HB8." J. Biol. Chem. 259:100041–47 (1984).
Takahashi, M., et al., "Thermophilic HB8 DNA ligase: effects of polyethylene glycols and polyamines on blunt–end ligation of DNA." J. Biochem. 100:123–131 (1986).
Wu, D., et al., "The ligation amplification reaction (LAR)—amplification of specific DNA sequenes using sequential rounds of template–dependent ligation." Genomics 4:560–569 (1989).
Barany, Proc. natl. Acad. Sic. USA, 88:189–193 (1991).
Takahashi et al, J. Biol. Chem., 259:10041–10047 (1984).
Pledger et al, J. Gen. Microbiol., 137:203–211 (1991).
Fiala et al, Arch. Microbiol., 145:56–61 (1986).
Bryant et al, J. Biol. Chem., 264:5070–5079 (1989).
J.M. Ward et al. Analytica Chimica Acta. 249:195–200 (1991).
R.C. Tait et al. J. Biol Chem. 255(3) 813–815 (1980.
S.B. Zimmerman et al. J. Biol Chem. 250(1) 149–155 (Jan. 1975).
M. Takahashi et al. Eur. J. Biochem. 192:735–740 (1990).
N. Oishi et al. J. Biochem. 95:1187–1192 (1984).
S. Hardy et al. Nuc. Acids Res. 19(4) 701–705 (Feb. 1991).
T. Lindahl methods. in Enzymology 21:333–338 (1971).
S.M. Panasanko et al. J. Biol. Chem. 253(13)4590–4592 (Jul. 1978).

Primary Examiner—Rebecca E. Prouty
Attorney, Agent, or Firm—Finnegan, Henderson, Farabow, Garrett & Dunner, L.L.P.

[57] ABSTRACT

Purified thermostable DNA ligase is described that catalyzes template-dependent ligation at temperatures of about 30° C. to about 80° C., and which substantially retains its catalytic ability when subjected to temperatures of from about 85° C. to about 100° C. The thermostable DNA ligase has an estimated molecular weight of 50,000 to 70,000 daltons. A preferred thermostable DNA ligase is described that was isolated from the archaebacteria Pyrococcus furiosus. Also described are plasmid vectors for producing recombinant thermostable DNA ligase.

3 Claims, 5 Drawing Sheets

5,700,672

PURIFIED THERMOSTABLE PYROCOCCUS FURIOUSUS DNA LIGASE

TECHNICAL FIELD

The present invention relates to a thermostable enzyme having DNA ligase activity useful in ligase chain reactions and other nucleic acid manipulations.

BACKGROUND

The hyperthermophiles of archaebacteria are a recently discovered group of microorganisms that grow optimally at temperatures around 100° C. Many species of these extremely thermophilic bacteria-like organisms have been isolated, mainly from shallow submarine and deep sea geothermal environments. Most of the archaebacteria are strict anaerobes and depend on the reduction of elemental sulfur for growth.

The "hyperthermophiles" are presently represented by three distinct genera, Pyrodictium, Pyrococcus, and Pyrobaculum. *Pyrodictium brockii* ($T_{opt}$ 105° C.) is an obligate autotroph which obtains energy by reducing $S^0$ to $H_2S$ with $H_2$, while *Pyrobaculum islandicum* ($T_{opt}$ 100° C.) is a facultative heterotroph that uses either organic substrates or $H_2$ to reduce $S^0$. In contrast, *Pyrococcus furiosus* ($T_{opt}$ 100° C.) grows by a fermentative-type metabolism rather than by $S^0$ respiration. It is a strict heterotroph that utilizes both simple and complex carbohydrates where only $H_2$ and $CO_2$ are the detectable products. The organism reduces elemental sulfur to $H_2S$ apparently as a form of detoxification since $H_2$ inhibits growth.

The discovery of microorganisms growing optimally around 100° C. has generated considerable interest in both academic and industrial communities. Both the organisms and their enzymes have the potential to bridge the gap between biochemical catalysis and many industrial chemical conversions. However, knowledge of the metabolism of the hyperthermophllic microorganisms is presently very limited.

The ligase chain reaction (LCR) provides a powerful method for the rapid and sensitive amplification of DNA fragments. LCR allows the specific detection of a target nucleic acid sequence with a single base mutation. LCR has facilitated the development of gene diagnostic technologies including the determination of allelic variation, and the detection of infectious and genetic disease disorders.

LCR is performed by repeated cycles of heat denaturation of a DNA template containing the target sequence, annealing a first set of two adjacent oligonucleotide probes to the target DNA sequence in a unique manner, and a second set of complementary oligonucleotide probes that hybridize to the sequence opposite to the target DNA sequence. Thereafter, a thermostable DNA ligase will covalently link each pair of adjacent probes provided there is complete complementarity at the junction of the two adjacent probes. Because the oligonucleotide products from one round may serve as substrates during the next round, the signal is amplified exponentially, analogous to the polymerase chain reaction (PCR).

LCR has been extensively described by Landegren et al., *Science*, 241:1077–1080 (1988); Wu et al., *Genomics*, 4:560–569 (1989); Barany, in *PCR Methods and Applications*, 1:5–16 (1991); and Barany, *Proc. Natl. Acad. Sci. USA*, 88:189–193 (1991).

An important aspect of successful LCR is to reduce background target-independent ligations, including blunt-end ligations. Such target-independent ligations produce a product the same size as the desired product from a target-directed LCR reaction, and as such are indistinguishable from the desired reaction product. The method requires a thermostable ligase to allow ligation to occur under temperature conditions that prevent mismatches from hybridizing to form acceptable substrates for a thermostable DNA ligase.

DNA ligases exhibiting limited temperature stability have been isolated from *Thermus aquaticus* (Taq), and from *Thermus thermophilus* (Tth). See, for example Takahashi et al., *J. Biol. Chem.*, 259:10041–10047 (1984). However, these enzymes do not maintain thermostability at temperatures greater than about 65° C. for prolonged periods of up to 10 to 30 minutes as required for typical LCR protocols. Thus, the known DNA ligases are unstable at high temperatures for prolonged periods, and therefore require a "pre-melt" step in LCR procedures to separate the two strands of the genomic DNA molecule prior to the addition of the enzyme followed by LCR cycles below about 85° C. to 90° C.

There continues to exist a need for a thermostable DNA ligase that can retain activity at high temperatures for prolonged periods of time, such as during ligase chain reactions.

SUMMARY OF THE INVENTION

A thermostable DNA ligase from hyperthermophilic marine archaebacterium species has been discovered. The monomeric enzyme possesses DNA ligase activity and is substantially free from target-independent ligation activity in ligase chain reactions. The ligase is extremely thermostable at 100° Centigrade (C), substantially retaining its catalytic activity after 30 minutes exposure to temperatures of about 85° C. to about 100° C., and has a catalytic activity range of about 30° C. to about 80° C., with an enzymatic activity temperature optimum of about 70° C.

The purified thermostable DNA ligase of this invention functions effectively in the ligase chain reaction (LCR) without catalyzing significant blunt-end ligation, and can be used without the limitations of thermo-instability during exposure to high temperatures during the LCR procedures. A thermostable DNA ligase of this invention can be utilized in LCR without the need to "pre-melt" the genomic DNA prior to LCR.

The apparent molecular weight of the native protein is about 50,000 to 70,000 daltons, and preferably about 55,000 to 65,000 daltons, as determined by SDS-PAGE under denaturing (reducing) conditions. Preferably, the thermostable DNA ligase has DNA ligase activity optimum in a pH range of 6–8, affording a wide range of hybridization conditions in which the enzyme is active. A preferred thermostable DNA ligase also binds rATP.

A preferred thermostable DNA ligase is isolated from *Pyrococcus furiosus* (Pfu) and is designated Pfu DNA ligase.

The invention also describes a plasmid containing a gene coding for a thermostable DNA ligase which catalyzes template-dependent ligation at temperatures of about 30° C. to about 80° C., and which substantially retains its catalytic activity when subjected to temperatures of from about 85° C. to about 100° C. The plasmid is useful for producing recombinant, purified, thermostable DNA ligase.

BRIEF DESCRIPTION OF THE DRAWINGS

In the drawings forming a portion of this disclosure.

DETAILED DESCRIPTION OF THE INVENTION

A. Definitions

Figure 1:
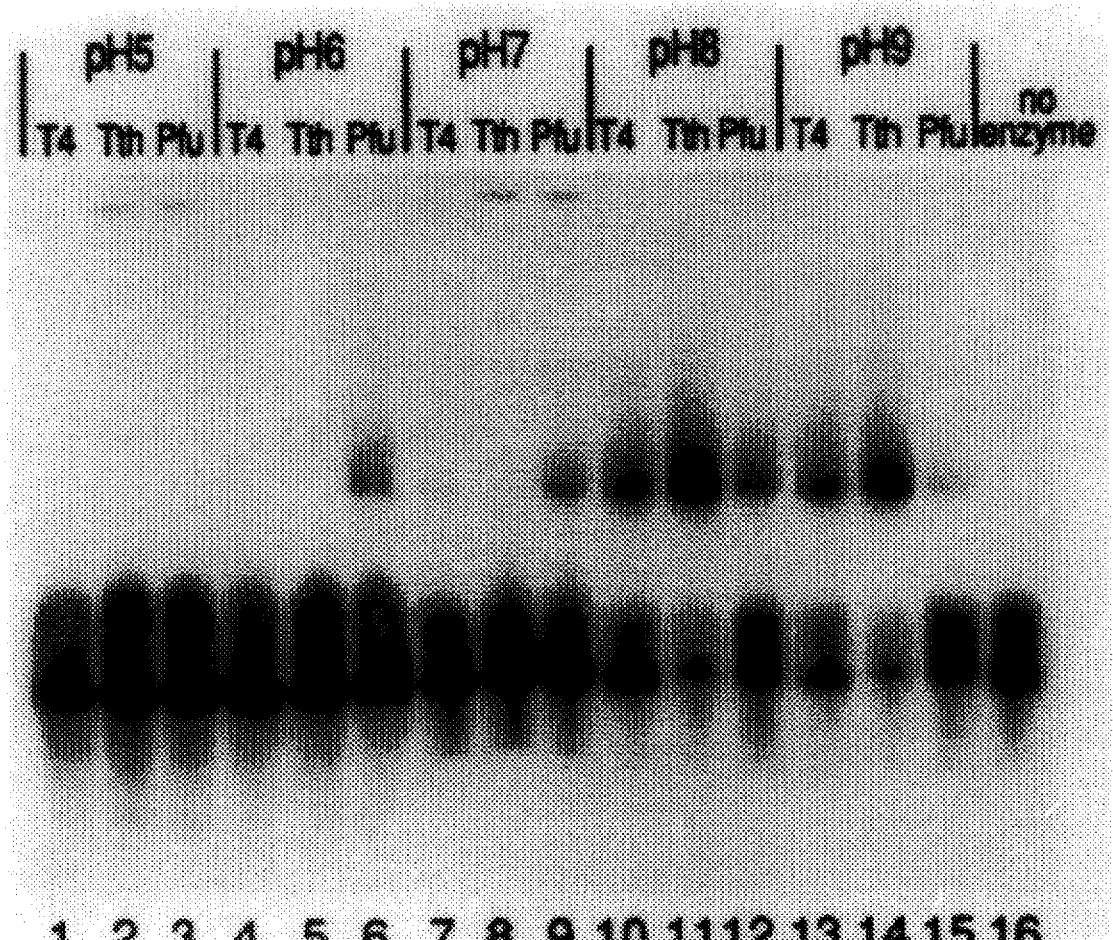
FIG. 1 illustrates an PAGE analysis of a nick sealing ligation activity assay that measures the pH-dependence of various DNA ligases as described in Example 3. Lanes 1–3 contain T4, Tth and Pfu DNA ligase, respectively, at pH 5. Lanes 4–6 contain T4, Tth and Pfu DNA ligase, respectively, at pH 6. Lanes 7–9 contain T4, Tth and Pfu DNA ligase, respectively, at pH 7. Lanes 10–12 contain T4, Tth and Pfu DNA ligase, respectively, at pH 8. Lanes 13–15 contain T4, Tth and Pfu DNA ligase, respectively, at pH 9. Lane contains a control incubation without enzyme at pH 8.

As used herein, "cell", "cell line", and "cell culture" can be used interchangeably and all such designations include progeny. Thus, the words "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included.

The term "control sequences" refers to DNA sequences necessary for the expression of an operably linked coding sequence in a particular host organism. The control sequences that are suitable for procaryotes, for example, include a promoter, optionally an operator sequence, a ribosome binding site, and the like. Eucaryotic cells are known to utilize promoters, polyadenylation signals, and enhancers.

The term "expression system" refers to DNA sequences containing a desired coding sequence and control sequences in operable linkage, so that hosts transformed with these sequences are capable of producing the encoded proteins. In order to effect transformation, the expression system may be included on a vector; however, the relevant DNA may then also be integrated into the host chromosome.

The term "gene" as used herein refers to a DNA sequence that encodes a polypeptide.

"Operably linked" refers to juxtaposition such that the normal function of the components can be performed. Thus, a coding sequence "operably linked" to control sequences refers to a configuration wherein the coding sequences can be expressed under the direction of the control sequences.

The term "oligonucleotide" as used herein is defined as a molecule comprised of two or more deoxyribonucleotides and/or ribonucleotides, preferably more than three. Its exact size will depend on many factors, which in turn depend on the ultimate function or use of the oligonucleotide. The oligonucleotide may be derived synthetically or by cloning.

The term "primer" as used herein refers to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, i.e., in the presence of four different nucleotide triphosphates and thermostable enzyme in an appropriate buffer ("buffer" includes pH, ionic strength, cofactors, etc.) and at a suitable temperature.

"Amino Acid Residue" as described herein are preferred to be in the "L" isomeric form. However, residues in the "D" isomeric form can be substituted for any L-amino acid residue, as long as the desired functional property is retained by the polypeptide. NH2 refers to the free amino group present at the amino terminus of a polypeptide. COOH refers to the free carboxy group present at the carboxy terminus of a polypeptide. The amino-terminal $NH_2$ group and carboxy-terminal COOH group of free polypeptides are typically not set forth in a formula. A hyphen at the amino- or carboxy-terminus of a sequence indicates the presence of a further sequence of amino acid residues or a respective $NH_2$ or COOH terminal group. In keeping with standard polypeptide nomenclature, *J. Biol. Chem.*, 243:3552–59 (1969) and adopted at 37 CFR §1.822(b) (2), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |

-continued

TABLE OF CORRESPONDENCE

| 1-Letter | SYMBOL 3-Letter | AMINO ACID |
|---|---|---|
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence", and is represented herein by a formula whose left to right orientation is in the conventional direction of 5'-terminus to 3'-terminus.

Base Pair (bp): A partnership of adenine (A) with thymine (T), or of cytosine (C) with guanine (G) in a double stranded DNA molecule.

B. Thermostable DNA Ligase

A thermostable DNA ligase of the present invention is an enzyme that catalyzes the template-dependent joining of two adjacent oligonucleotide probes while substantially hybridized to the template. The thermostable DNA ligase is free from significant blunt end ligation activity when measured in an LCR of at least 30 cycles, as described herein.

As used herein, the term "thermostable DNA ligase" in the context of this invention refers to an enzyme which:

(1) is stable, i.e., substantially retains enzymatic activity, upon exposure to heat at temperatures above 70° C., preferably above 90° C., and more preferably above 99° C., and (2) catalyzes (facilitates) combination (ligation) of the nucleotides by formation of covalent phosphodiester bond in a template-dependent manner to form a ligation reaction product.

Stated differently, the thermostable DNA ligase enzyme herein must not become irreversibly denatured (inactivated) when subjected to the elevated temperatures for the time necessary to effect separation of double-stranded nucleic acids, and preferably not inactivated when repeatedly subjected to those elevated temperatures, as in the repetition utilized in LCR. More preferably, the thermostable DNA ligase substantially retains its activity under conditions of high temperature.

By substantially retains is meant that greater that 50%, preferably greater that 80%, and more preferably more than 95%, of the enzymatic activity is preserved after exposure to 100° C. for 30 minutes. Assays useful for monitoring temperature stability are described in the Examples.

In preferred embodiments, these elevated temperatures are in the range of 80° C.–100° C., and preferably are in the range of 95° C.–100° C. Preferably, these elevated temperatures can be maintained continuously for at least 5 minutes, preferably for at least 10 minutes, and more preferably for at least 30 minutes without detectable diminution in activity using the methods described herein.

The heating conditions necessary for strand separation will depend, e.g., on the buffer salt concentration and the length and nucleotide composition of the nucleic acids being separated, but typically range from about 90° C. to about 100° C. for a time depending mainly on the temperature and the nucleic acid length, typically about 0.5 to four minutes. Higher temperatures may be necessary as the buffer salt concentration and/or GC composition of the nucleic acid is increased.

The thermostable DNA ligase of the invention preferably has a temperature range in which it is enzymatically active of about 30° C. to 80° C. (i.e., thermoactivity), and preferably has a temperature optimum for maximum enzyme activity of about 70° C.

A thermostable DNA ligase of the invention preferably has a temperature range in which it is stable (i.e., thermostability) when exposed to that temperature after prolonged periods (i.e., 5 minutes to 1 hour), which temperature is preferably greater than 80° C., and more preferably about 95° C. to 100° C. This temperature stability range is particularly preferred because it allows for the cycling of temperatures, as in LCR, over a range of temperatures, including a high temperature sufficient to insure greater hybridization specificity and/or selectivity of the oligonucleotide probe-directed ligation process.

Ligation is template-dependent when there is no significant amount of blunt end ligation, and where efficient ligation depends on the presence of duplex DNA at the site of the single strand nick to be joined by the ligase. Stated differently, template dependent ligation is ligation that requires that the two adjacent single-stranded DNA molecules to be covalently linked by a phosphodiester bond are each substantially hybridized to a complementary single-stranded DNA molecule. Exemplary template-dependent ligation is shown in the Examples using two oligonucleotides having sequences selected to be completely complementary with a template oligonucleotide.

By substantially hybridized is meant that the ligation conditions are conducted under conditions that favor a hybridized (double-stranded) DNA molecule rather than non-hybridized (single-stranded) DNA molecules. Preferably, more that 50% of the nucleotide bases of each strand of DNA molecule, preferably more than 80%, and more preferably greater than 95%, are participating in hydrogen bonding characteristic of duplex DNA. More preferably, substantially all (about 100%) nucleotide bases are hybridized.

A thermostable DNA ligase of the invention preferably has the ability to bind rATP under the conditions described and demonstrated for Pfu DNA ligase in Example 6.

A thermostable DNA ligase of the invention preferably exhibits DNA ligase activity in a range of pH conditions from ph 6 to pH 8.

Pfu DNA ligase is suitable for use in a ligase chain reaction (LCR) in a buffer that preferably contains 1–50 mM of a magnesium salt, preferably $MgCl_2$, 0–100 mM KCl, preferably 10 mM, 0–50 mM $NH_4Cl$, preferably 10 mM, 0.1–10 mM dithiothreitol (DTT), preferably 1 mM, along with 0.1–1M buffer, preferably 1–100 mM, and more preferably 50 mM bis-Tris pH 6.5, and a stabilizer, preferably 100 µg/ml gelatin.

A thermostable DNA ligase of the present invention can be obtained from any source and can be a native or recombinant protein.

A preferred thermostable DNA ligase is any one of the DNA ligases obtainable from a species of hyperthermophillic archaebacteria selected from the group consisting of *Pyrodictium occultum, Pyrodictium abssyum, Thermodiscus maritumus, Thermococcus celer, Thermococcus litoralis, Thermococcus stetteri, Pyrococcus furiosus, Staphylothermus marinus,* Desulfurococcus, *Archaeoglobus profundus, Hyperthermus butylicus, Archaeoglobus fulgidus,* Pyrococcus strain GB-D, and archaebacteria strains AL-1, AL-2, ES-1 and ES-2. Strains Al-1, AL-2, ES-1 and ES-4 have been isolated and described by John Baross. See, for example, Pledger et al., *J. Gen. Microbiol.,* 137:203–211, 1991.

A particularly preferred thermostable DNA ligase is the DNA ligase isolated from *Pyrococcus furiosus* (Pfu) that is designated herein as Pfu DNA ligase. *P. furiosus* is available from Dentsche Sammlung Von Microorganismen (DSM), Grise-Bach StraSSE 8, d-3400 Göttengen, FRG, under the accession number DSM-6217.

For isolating the native protein from *P. furiosus* cells, such cells are grown using any suitable technique. A variety of such techniques have been reported, those preferred being described by Fiala et al., *Arch. Microbiol,* (1986) 145:56–61, and Bryant et al., *J. Biol. Chem.,* (1989) 264:5070–5079, the disclosures of which are incorporated herein by reference. Particularly preferred are the methods described herein.

After cell growth, the isolation and purification of Pfu DNA ligase is performed at, and preferably below, room temperature, preferably about 4° C.

In the first step, the cells are concentrated from the growth medium, typically by centrifugation or filtration. In preferred isolation procedures, all buffers contain a stabilizing agent, such as 10% glycerol or the like, to increase the activity and yield of a DNA ligase preparation produced by the present methods.

In the second step, the cells are lysed and the supernatant is segregated and recovered from the cellular debris. Lysis is typically accomplished by mechanically applying sheer stress and/or enzymatic digestion. Segregation of the supernatant is usually accomplished by centrifugation.

The third step removes nucleic acids and some protein. The supernatant from the second step is applied to an agarose resin strong anionic exchange column, such as Q-sepharose from Pharmacia (Piscataway, N.J.) equilibrated with column buffer [50 mM tris-hydroxymethylaminomethane (Tris), pH 8.0, 10 mM dithiothreitol (DTT), 0.1% NP-40, 0.1% Tween-20, 10% glycerol and 0.1 mM ethylenediaminetetraacetic acid (EDTA)]. The column is washed with column buffer to remove unwanted macromolecules, and the Pfu DNA ligase remains bound to the Q-sepharose column resin. The bound protein is then eluted off the column with the column buffer in a linear gradient of 0–0.5 molar (M) KCl, with the Pfu DNA ligase eluting at about 0.25M KCl. The eluant fractions are collected and centrifuged to remove any insoluble material. The collected eluant is segregated, usually dialyzed, and then recovered to form a fraction containing partially purified Pfu DNA ligase.

The fourth step removes substantially all (90%) of the remaining contaminating proteins and comprises applying the fraction recovered from step three to a phosphocellulose column equilibrated with the before described column buffer adjusted to pH 6.5. The column is washed with the column buffer until the optical density of the wash eluate is at the buffer baseline at 280 nm. The immobilized Pfu DNA ligase is thereafter eluted with a linear salt gradient comprising 0.0M to about 1.0M KCl salt dissolved in the column buffer. Protein eluted from the column at about 500 mM salt typically contains the highest concentrations of assayable Pfu DNA ligase.

In preferred embodiments, the Pfu DNA ligase preparation obtained from the fourth step is further purified in a fifth step by FPLC chromatography through a high performance cation exchange column, such as the HiLoad S column available from Pharmacia, Piscataway, N.J., equilibrated with the before described column buffer at pH 6.5. After application, the column is washed to remove non-bound contaminants. The immobilized Pfu DNA ligase is then eluted with the before-described 0.0–0.5M KCl linear salt gradient at about 120 mm salt concentration. The Pfu DNA ligase eluate is then typically dialyzed against the column buffer to remove excess salt. Additional stabilizing agent, such as glycerol, is preferably added to the preparation at this time to increase the stabilizer effectiveness to facilitate low temperature storage. Preferred low temperature storage amounts of stabilizer are about 50% weight per volume of glycerol, or its equivalents. Typically, the fraction is again dialyzed against a low salt buffer, e.g., 50 mM Tris pH 7.5, 1 mM dithiothreitol, 0.1 mM EDTA, 0.1% Tween 20, and 0.1% non-idet P40.

The amino-terminal amino acid residue sequence of a thermostable DNA ligase can be determined by any suitable method, such as by automated Edman degradation, and the like. The amino acid residue sequence of the preferred Pfu DNA ligase includes the amino acid residue sequence shown in SEQ ID NO 1 from residue 1 to 50. Particularly preferred is a thermostable DNA ligase that includes the sequence shown in SEQ ID NO 1 from residue 1 to residue 553.

Insofar as amino acid modifications, substitutions, deletions or additions may be made to a thermostable DNA ligase without substantially altering its catalytic activity or thermostability, such changes in sequence are acceptable, and preferable, where such changes impart desirable characteristics upon the enzyme.

The molecular weight of the isolated thermostable DNA ligase product can be determined by any technique, for example, by sodium dodecylsulfate-polyacrylamide gel electrophoresis (SDS-PAGE) using protein molecular weight markers. Native Pfu DNA ligase purified by the above method has a relative molecular weight, determined by SDS-PAGE under reducing conditions, of about 55,000 to 65,000 daltons, and preferably has a molecular weight of from about 58,000 to 64,000 daltons, as determined in Example 9.

C. Recombinant Thermostable DNA Ligase

A thermostable DNA ligase of this invention can also be produced by recombinant DNA (rDNA) techniques, as the gene encoding the enzyme can be cloned from the genome of a thermophilic archaebacteria described herein. Preferably, a thermostable DNA ligase is cloned from *P. furiosus* genomic DNA. Thus, the present invention also contemplates a DNA segment consisting essentially of a sequence of nucleotide base sequence encoding a thermostable DNA ligase, and preferably a Pfu DNA ligase, of this invention.

An exemplary DNA segment, obtained from the native gene, and coding for a portion of a preferred Pfu ligase protein is shown in SEQ ID NO 2 from nucleotide base 106 to base 1767, which spans the coding portion of SEQ ID NO 2.

A preferred DNA segment having a sequence that encodes a Pfu DNA ligase of this invention is present on the BamHI to SalI fragment of the plasmid vector pEM1 described herein.

Plasmid pEM1 has been deposited pursuant to Budapest Treaty requirements with the American Type Culture Collection (ATCC), Rockville, Md., on Jul. 1, 1992, and was assigned accession number 75259.

Plasmid pEM1 was deposited in a depository affording permanence of the deposit and ready accessibility thereto by the public upon the issuance of a patent, under conditions which assure that access to the plasmid will be available during the pending of the patent application to those deemed by the Commissioner to be entitled to such access, and that all restrictions on the availability to the public of the plasmid as deposited will be irrevocably removed upon the granting of the patent. The deposited plasmid will be maintained by the ATCC for the term of the patent or 30 years from the date of deposit, whichever is longer, and in all events for at least five years after the date of the last request for access.

Also contemplated are DNA segments that encode a thermostable DNA ligase of this invention. In view of the unique nature of the thermostable DNA ligase described herein, and the significant nucleotide sequence difference of a gene that encodes for Pfu DNA ligase when compared to E. coli or Tth DNA ligase, it is apparent that a highly homologous nucleotide sequence, when compared to the nucleic acid sequence encoding Pfu DNA ligase, is a thermostable DNA ligase of the present invention. "High homology" is defined as two nucleotide sequences that share greater than 50% identity in their nucleotide sequence, preferably greater than 80%, and more preferably greater than 90%, identity.

Stated differently, "high homology" exists where an isolated DNA segment, in single stranded form, hybridizes to another single stranded DNA segment under high stringency conditions. Typical high stringency DNA hybridization conditions are generally well known, and are preferably conditions that require the degrees of nucleotide sequence identity for a hybridization product to form to be in excess of those recited previously. Exemplary and preferred high stringency conditions are described in the hybridization conditions described in the Examples.

Thus the invention also contemplates an isolated DNA segment that codes for a thermostable DNA ligase of this invention. The DNA segment can have a nucleotide sequence that hybridizes under high stringency conditions to a DNA segment having a DNA sequence according to SEQ ID NO 2, and preferably is identical to the sequence according to SEQ ID NO 2.

In a related embodiment, the invention contemplates a thermostable DNA ligase according to the present invention having an amino acid residue sequence coded by the above DNA segment.

In a related embodiment, an isolated gene encoding a thermostable DNA ligase of this invention can be operably linked to an expression system to form an rDNA capable of expressing, in a compatible host, a thermostable DNA ligase of this invention. Particularly preferred is an rDNA that encodes Pfu DNA ligase. Exemplary vectors and expression are described herein.

Of course, modifications to the primary structure itself by deletion, addition, or alteration of the amino acids incorporated into the protein sequence during translation can be made without destroying the activity of the protein. Such substitutions or other alterations result in proteins having an amino acid sequence encoded by DNA falling within the contemplated scope of the present invention.

In one embodiment, the DNA segment coding for a thermostable DNA ligase can be operatively linked to additional coding sequences in a manner that forms a fusion protein comprising heterologous amino acid residue sequences operatively linked by amide bond to the amino acid residue sequence that defines a thermostable DNA ligase. An exemplary fusion protein is described in Example 10 and has cloned nucleotide sequences encoding Pfu DNA ligase fused to sequences encoding portions of the beta-galactosidase gene.

Recombinant Pfu DNA ligase is purified from cultures of host cells expressing the recombinant protein as described earlier herein, or can be purified as described in Example 11.

1. Cloning and Expression of the Pfu DNA Ligase Gene

In one embodiment, a purified thermostable DNA ligase can be used to determine partial amino-terminus amino acid residue sequence data, as was done herein in Example 10. Thus applying the DNA ligase purification methods, one can obtain purified thermostable DNA ligase, and determine the amino acid residue sequence of the amino termini suitable to construct nucleotide probes for screening a genomic library.

Particularly preferred is the method of identifying the amino termini, followed by developing primer extension oligonucleotides for use after the amino terminal sequence is determined to support "vectorette cloning" as described herein.

Accordingly, portions of the genomic DNA encoding at least six contiguous amino acids can be synthesized and used as probes to retrieve additional DNAs encoding an Archaebacteria thermostable ligase. Because there may not be a precisely exact match between the nucleotide sequence in the P. furiosus form described herein and that in the corresponding portion of other species or strain, oligomers containing approximately 18 nucleotides (encoding the six amino acid stretch) are necessary to obtain hybridization under conditions of sufficient stringency to eliminate false positives. The sequences encoding six amino acids supplies information sufficient for such probes.

Alternatively, polyclonal antiserum from rabbits immunized with purified Pfu DNA ligase of this invention can be used to probe a P. furiosus partial genomic expression library to obtain the appropriate coding sequence as described below. The cloned genomic sequence can be expressed as a fusion protein, expressed directly using its own control sequences, or expressed by constructions using control sequences appropriate to the particular host used for expression of the enzyme.

Thus, the complete coding sequence for a thermostable DNA ligase from which expression vectors applicable to a variety of host systems can be constructed and the coding sequence expressed. It is also evident from the foregoing that portions of the Pfu DNA ligase-encoding sequence are useful as probes to retrieve other similar thermostable ligase-encoding sequences in a variety of archaebacteria species described herein, such as Pyrodictium occultum, Pyrodictium abssyum, Thermodiscus maritumus, Thermococcus celer, Thermococcus litoralis, Thermococcus stetteri, Pyrococcus furiosus, Staphylothermus marinus, Desulfurococcus, Archaeoglobus profundus, Hyperthermus butylicus, Archaeoglobus fulgidus, Pyrococcus strain GB-D, and archaebacteria strains AL-1, AL-2, ES-1 and ES-2. Particularly preferred sources of a coding sequence for a thermostable DNA ligase of this invention are other Pyrococcus species and P. furiosus strains.

A preferred and exemplary cloning protocol for isolation of a pfu ligase gene is described in the Examples. From the clone pEM1 described in the Examples, the nucleotide sequence of a preferred gene encoding Pfu DNA ligase was described and is shown in SEQ ID NO 2, and can be utilized for the production of recombinant Pfu DNA ligase.

In general terms, the production of a recombinant form of Pfu DNA ligase typically involves the following:

First, a DNA is obtained that encodes the mature (used here to include all muteins) enzyme or a fusion of the Pfu DNA ligase either to an additional sequence that does not destroy its activity, or to an additional sequence cleavable under controlled conditions (such as treatment with peptidase) to give an active protein. If the sequence is uninterrupted by introns it is suitable for expression in any host. This sequence should be in an excisable and recoverable form.

The excised or recovered coding sequence is then preferably placed in operable linkage with suitable control sequences in a replicable expression vector. The vector is used to transform a suitable host and the transformed host cultured under favorable conditions to effect the production of the recombinant Pfu DNA ligase. Optionally the Pfu DNA ligase is isolated from the medium or from the cells; recovery and purification of the protein may not be necessary in some instances, where some impurities may be tolerated.

Each of the foregoing steps can be done in a variety of ways. For example, the desired coding sequences may be obtained from genomic fragments and used directly in appropriate hosts. The constructions for expression vectors operable in a variety of hosts are made using appropriate replicons and control sequences, as set forth below. Suitable restriction sites can, if not normally available, be added to the ends of the coding sequence so as to provide an excisable gene to insert into these vectors.

The control sequences, expression vectors, and transformation methods are dependent on the type of host cell used to express the gene. Generally, procaryotic, yeast, insect or mammalian cells are presently useful as hosts. Procaryotic hosts are in general the most efficient and convenient for the production of recombinant proteins and therefore are preferred for the expression of Pfu DNA ligase.

2. Control Sequences and Corresponding Hosts

Procaryotes most frequently are represented by various strains of *E. coli*. However, other microbial strains may also be used, such as bacilli, for example, Bacillus subtillis, various species of Pseudomonas, or other bacterial strains. In such procaryotic systems, plasmid vectors that contain replication sites and control sequences derived from species compatible with the host are used. For example, *E. coli* is typically transformed using derivatives of pBR322, a plasmid derived from an *E. coli* species by Bolivar et al., *Gene*, 2:95 (1977); and Sutcliffe, *Nuc. Acids Res.*, 5:2721–28 (1978). pBR322 contains genes for ampicillin and tetracycline resistance, and thus provides additional markers that can be either retained or destroyed in constructing the desired vector. Commonly used procaryotic control sequences, which are defined herein to include promoters for transcription initiation, optionally with an operator, along with ribosome binding site sequences, include such commonly used promoters as the B-lactamase (penicillinase) and lactose (lac) promoter systems (Chang et al., *Nature*, 198:1056, 1977), the tryptophan (trp) promoter system (Goeddel et al., *Nucleic Acids Res.*, 8:4057, 1980) and the lambda-derived $P_L$ promoter (Shimatake et al., *Nature*, 292:128, 1981) and N-gene ribosome binding site ($N_{RBS}$), which has been made useful as a portable control cassette (as set forth in U.S. Pat. No. 4,711,845), which comprises a first DNA sequence that is the $P_L$ promoter operably linked to a stream of a third DNA sequence having at least one restriction site that permits cleavage with six bp 3' of the $N_{RBS}$ sequence. Also useful is the phosphatase A (phoA) system described by Change et al. in European Patent Publication No. 196,864. However, any available promoter system compatible with procaryotes can be used. Typical bacterial plasmids are pUCS, pUC9, pBR322 and pBR329 available from Bio-Rad Laboratories, (Richmond, Calif.) and pPL and pkk233-2, available from Pharmacia (Piscataway, N.J.) or Clone Tech (Palo Alto, Calif.).

In addition to bacteria, eucaryotic microbes, such as yeast, may also be used as hosts. Laboratory strains of *Saccharomyces cerevisiae*, Baker's yeast, are most used, although a number of other strains are commonly available. While vectors employing the 2 micron origin of replication are illustrated (Broach, *Meth. Enz.*, 101:307, 1983), other plasmid vectors suitable for yeast expression are known (see, for example, Stinchcomb et al., *Nature*, 282:39, 1979; Tschempe et al., *Gene*, 10:157, 1980; Clarke et al., *Meth. Enz* 101:300, 1983; Brake et al., *Proc. Natl. Acad. Sci. USA*, 81:4642–4647, 1984; and Halewell et al., *Biotechnology*, 5:363–366, 1987) . Control sequences for yeast vectors include promoters for the synthesis of glycolytic enzymes (Hess et al., *J. Adv. Enzyme Reg.*, 7:149, 1968; Holland et al., *Biotechnology* 17:4900, 1978).

Additional promoters known in the art include the promoter for 3-phosphoglycerate kinase (Hitzeman et al., *J. Biol. Chem.*, 255:2073, 1980) and those for other glycolytic enzymes, such as glyceraldehyde-3phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters that have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization (Holland, supra).

It is also believed that terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland et al., *J. Biol Chem.*, 256:1385, 1981) or the LEU2 gene obtained from YEp13 (Broach et al., *Gene*, 8:21, 1978); however, any vector containing a yeast-compatible promoter, origin of replication, and other control sequences is suitable.

It is also, of course, possible to express genes encoding polypeptides in eucaryotic host cell cultures derived from multicellular organisms. See, for example, *Tissue Culture*, Academic Press, Cruz and Patterson, editors (1973). Useful host cell lines include murine myelomas N51, VERO and HeLA cells, and Chinese hamster ovary (CHO) cells available from the ATCC as CCL61, and NIH/3T3 mouse cells available from the ATCC as CRL1658. Expression vectors for such cells ordinarily include promoters and control sequences compatible with mammalian cells such as, for example, the commonly used early and late promoters from Simian Virus 40 (SV 40) (Fiers et al., *Nature*, 273:113, 1978), or other viral promoters such as those derived from polyoma, Adenovirus 2, bovine papilloma virus, or avian sarcoma viruses, or immunoglobulin promoters and heat shock promoters. A system for expressing DNA in mammalian systems using the BPV as a vector is disclosed in U.S. Pat. No. 4,419,446. A modification of this system is described in U.S. Pat. No. 4,601,978. General aspects of mammalian cell host system transformations have been described in U.S. Pat. No. 4,399,216. It now appears, also, that "enhancer" regions are important in optimizing expression; these are, generally, sequences found upstream of the promoter region. Origins of replication may be obtained, if needed, from viral sources. However, integration into the chromosome is a common mechanism for DNA replication in eucaryotes.

Plant cells are also now available as hosts, and control sequences compatible with plant cells such as the nopaline synthase promoter and polyadenylation signal sequences (Depicker et al., *J. Mol. Appl. Gen.*, 1:561, 1982) are available. See, also, U.S. Pat. Nos. 4,962,028, 4,956,282, 4,886,753 and 4,801,540.

Recently, in addition, expression systems employing insect cells utilizing the control systems provided by baculovirus vectors have been described (Miller et al., in *Genetic Engineering*, Setlow, J. K. et al., eds., Plenum Publishing, Vol. 8, pp. 277–297, 1986). See, also, U.S. Pat. Nos. 4,745,051 and 4,879,236. These systems are also successful in producing Pfu DNA ligase.

A preferred DNA segment containing both the Pfu ligase coding portion and control sequences at the 5' and 3' termini of the coding portion is present on the BamHI to SalI fragment of plasmid pEM1 described in Example 10 and includes a nucleotide sequence shown in SEQ ID NO 2 from nucleotide base 106 to base 1767.

3. Transformations

The recombinant DNA molecules of the present invention are introduced into host cells, via a procedure commonly known as transformation or transfection. Transformation of appropriate host cells with a recombinant DNA molecule of the present invention is accomplished by well known methods that typically depend on the type of vector used. For descriptions of transformation of procaryotic host cells or other cells that contain substantial cell wall barriers, see, for example, Cohen et al., *Proc. Natl. Acad. Sci. USA*, 69:2110 (1972); and Maniatis et al., *Molecular Cloning, A Laboratory Manual*, Cold Spring Harbor Laboratory, Cold Spring Harbor, N.Y. (1982). For descriptions of transformation of vertebrate cells with retroviral vectors containing rDNA, see, for example, Sorge et al., *Mol. Cell. Biol.*, 4:1730–37 (1984); and Wigler et al., *Proc. Natl. Acad. Sci. USA*, 76:1373–76 (1979).

Infection with Agrobacterium tumefaciens (Shaw et al., *Gene*, 23:315, 1983) is used for certain plant cells. For mammalian cells without cell walls, the calcium phosphate precipitation method of Graham et al., *Virology* 52:546 (1978), is preferred. Transformations into yeast are carried out according to the method of Van Solingen et al., *J. Bact.*, 130:946 (1977); and Hsiao et al., *Proc. Natl. Acad. Sci. (USA)*, 76:3829 (1979).

Successfully transformed cells, i.e., cells that contain a recombinant DNA (rDNA) molecule of the present invention, are usually monitored by an appropriate immunological, hybridization or functional assay. For example, cells resulting from the introduction of an rDNA of the present invention can be cloned to produce monoclonal colonies. Cells from those colonies can be harvested, lysed and their DNA content examined for the presence of the rDNA using a method such as that described by Southern, *J. Mol. Biol.*, 98:503 (1975) or Berent et al., *Biotech.*, 3:208 (1985).

In addition to directly assaying for the presence of rDNA, successful transformation can be confirmed by well known immunological methods when the rDNA is capable of directing the expression of Pfu DNA ligase. For example, cells successfully transformed with a subject rDNA containing an expression vector produce a polypeptide displaying a characteristic antigenicity. Samples of a culture containing cells suspected of being transformed are harvested and assayed for a subject polypeptide (Pfu DNA ligase) using antibodies specific for that polypeptide antigen, such as those produced by an appropriate hybridoma.

A particularly convenient assay technique involves fusing the Pfu DNA ligase-encoding DNA to a Lac Z gene in a suitable plasmid, e.g. pLG. Since the plasmid lacks a promoter and Shine-Dalgarno sequence, no β-galactosidase is synthesized. However, when a portable promoter fragment is properly positioned in front of the fused gene, high levels of a fusion protein having β-galactosidase activity should be expressed. The plasmids are used to transform Lac-bacteria which are scored for β-galactosidase activity on lactose indicator plates. Plasmids having optimally placed promoter fragments are thereby recognized. These plasmids can then be used to reconstitute the fusion protein gene which is expressed at high levels.

Thus, in addition to the transformed host cells themselves, cultures of the cells are contemplated as within the present invention. The cultures include monoclonal (clonally homogeneous) cultures, or cultures derived from a monoclonal culture, in a nutrient medium. Nutrient media useful for culturing transformed host cells are well known in the art and can be obtained from several commercial sources. In embodiments wherein the host cell is mammalian, a "serum-free" medium is preferably used.

The present method entails culturing a nutrient medium containing host cells transformed with a recombinant DNA molecule of the present invention that is capable of expressing a gene encoding a subject polypeptide. The culture is maintained for a time period sufficient for the transformed cells to express the subject polypeptide. The expressed polypeptide is then recovered from the culture.

Once a gene has been expressed in high levels, a DNA fragment containing the entire expression assembly, e.g., promoter, ribosome-binding site, and fusion protein gene) may be transferred to a plasmid that can attain very high copy numbers. For instance, the temperature-inducible "runaway replication" vector pKN402 may be used. Preferably, the plasmid selected will have additional cloning sites which allow one to score for insertion of the gene assembly. See, Bittner et al., *Gene*, 15:31 (1981). Bacterial cultures transformed with the plasmids are grown for a few hours to increase plasmid copy number, e.g., to more than 1000 copies per cell. Induction may be performed in some cases by elevated temperature and in other cases by addition of an inactivating agent to a repressor. Potentially very large increases in cloned fusion proteins can be obtained in this way.

4. Recombinant DNA Molecules

The present invention further contemplates a recombinant DNA (rDNA) that includes a thermostable DNA ligase-encoding DNA segment of the present invention operatively linked to a vector for replication and/or expression. Preferred rDNA molecules contain less than 50,000 nucleotide base pairs, usually less than 20,000 base pairs and preferably less than about 10,000 base pairs. Preferably, a thermostable DNA ligase-encoding DNA of this invention is in the form of a plasmid, cosmid or phage.

A preferred rDNA molecule encodes a Pfu thermostable DNA ligase of this invention, and more preferably includes the fragment of plasmid pEM1 described in Example 10, and still more preferably includes a nucleotide sequence shown in SEQ ID NO 2 from nucleotide base 106 to base 1767.

A rDNA molecule of the present invention can be produced by operatively linking a vector to a DNA segment of the present invention.

As used herein, the term "vector" refers to a nucleic acid molecule capable of transporting between different genetic environments another nucleic acid to which it has been operatively linked Preferred vectors are those capable of autonomous replication and/or expression of nucleic acids to which they are operatively linked are referred to herein as "expression vectors". As used herein, the term "operatively linked", in reference to DNA segments, describes that the nucleotide sequence is joined to the vector so that the sequence is under the transcriptional and translation control of the expression vector and can be expressed in a suitable host cell.

As is well known in the art, the choice of vector to which a protein encoding DNA segment of the present invention is operatively linked depends upon the functional properties desired, e.g., protein expression, and upon the host cell to be transformed. These limitations are inherent in the art of constructing recombinant DNA molecules. However, a vector contemplated by the present invention is at least capable of directing the replication, and preferably also expression, of a gene operatively linked to the vector.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon may also include a gene whose expression confers a selective advantage such as amino acid nutrient dependency or drug resistance to a bacterial host transformed therewith as is well known, in order to allow selection of transformed clones. Typical bacterial drug resistance genes are those that confer resistance to ampicillin, tetracycline, or kanamycin.

Those vectors that include a procaryotic replicon may also include a procaryotic promoter capable of directing the expression (transcription and translation) of the gene transformed therewith. A promoter is an expression control element formed by a DNA sequence that permits binding of RNA ligase and transcription to occur. Promoter sequences compatible with bacterial hosts are typically provided in plasmid vectors containing convenient restriction sites for insertion of a DNA segment of the present invention. Bacterial expression systems, and choice and use of vectors in those systems is described in detail in "Gene Expression Technology", Meth. Enzymol., Vol 185, Goeddel, Ed., Academic Press, New York (1990).

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired gene. Typical of such vectors are pSVL and pKSV-10 (Pharmacia), pBPV-1/pML2d (International Biotechnologies, Inc.), and pTDT1 (ATCC, #31255).

In preferred embodiments, the eucaryotic cell expression vectors used to construct the recombinant DNA molecules of the present invention include a selectable phenotypic marker that is effective in a eucaryotic cell, such as a drug resistance selection marker or selective marker based on nutrient dependency. A preferred drug resistance marker is the gene whose expression results in neomycin resistance, i.e., the neomycin phosphotransferase (neo) gene. Southern et al., J. Mol. Appl. Genet., 1:327–341 (1982).

The use of retroviral expression vector to form the rDNAs of the present invention is also contemplated. As used herein, the term "retroviral expression vector" refers to a DNA molecule that includes a promoter sequence derived from the long terminal repeat (LTR) region of a retrovirus genome.

In addition to using strong promoter sequences to generate large quantities of mRNA coding for the expressed fusion proteins of the present invention, it is desirable to provide ribosome-binding sites in the mRNA to ensure efficient translation. The ribosome-binding site in E. coli includes an initiation codon (AUG) and a sequence 3–9 nucleotides long located 3–11 nucleotides upstream from the initiation codon (the Shine-Dalgarno sequence). See, Shine et al., Nature, 254:34 (1975). Methods for including a ribosome-binding site in mRNAs corresponding to the expressed proteins are described by Maniatis, et al. Molecular Cloning: A Laboratory Manual, Cold Spring Harbor Laboratory Press, N.Y. pp. 412–417 (1982). Ribosome binding sites can be modified to produce optimum configuration relative to the structural gene for maximal expression of the structural gene. Halewell et al., Nucl. Acid Res., 13:2017–2034 (1985).

Construction of suitable vectors containing the desired coding and control sequences employs standard ligation and restriction techniques that are well understood in the art. Isolated plasmids, DNA sequences, or synthesized oligonucleotides are cleaved, tailored, and religated in the form desired.

The preferred expression vector for producing recombinant Pfu DNA ligase is pEM1, which is described in Example 10, according to the expression and purification methods described in Example 11.

The thermostable enzyme of this invention may be used for any purpose in which such enzyme is necessary or desirable. In a particularly preferred embodiment, the enzyme herein is employed in the ligase chain reaction protocol set forth below.

EXAMPLES

The following examples are intended to illustrate, but not limit, the present invention.

1. Culturing of *Pyrococcus furiosus* and Preparation of Pfu Cell Paste

The following describes how the hyperthermophilic archaebacterium, *P. furiosus*, is routinely grown in a 500 liter fermentor for the purpose of obtaining cell mass in sufficient quantities for large scale protein purification. It is a modified version [Bryant et al., J. Biol. Chem., 264:5070–5079 (1989)] of the original protocol of Fiala et al., Arch. Microbiol., 145:56–61 (1986).

For culture maintenance, *P. furiosus* (DSM 3638) is routinely grown at 85° C.–88° C. as a closed static culture in 100 ml of the medium described in Table 2.

TABLE 2

| Maltose | 5 g/l |
|---|---|
| NH$_4$Cl | 1.25 g/l |
| Elemental Sulfur | 5 g/l |
| Na$_2$S | 0.5 g/l |
| Synthetic Sea Water[1] | |
| Vitamin mixture[2] | 1 ml/l |
| FeCl$_3$ | 25 µM |
| Na$_2$WO$_4$ | 10 µM |
| Yeast Extract | 0.01% |

[1]Synthetic Sea Water:
NaCl, 13.8 g/l
MgSO$_4$, 3.5 g/l
MgCl$_2$, 2.7 g/l
KCl, 0.3 g/l
CaCl$_2$, 0.75 g/l
KH$_2$PO$_4$, 0.5 g/l
NaBr, 0.0–5 g/l
KI, 0.05 g/l
H$_3$BO$_3$, 0.015 g/l
Sodium citrate, 0.005 g/l
[2]Vitamin mixture [Balch et al., Microbiol. Rev., 43:260–296 (1979)]:
Biotin, 2 mg/l
Folic acid, 2 mg/l
Pyridoxine hydrochloride, 10 mg/l
Thiamine hydrochloride, 5 mg/l
Riboflavin, 5 mg/l
Nicotinic acid, 5 mg/l
DL-Calcium pantothenate, 5 mg/l
Vitamin B$_{12}$, 0.1 mg/l
p-Aminobenzoic acid, 5 mg/l
Lipoic acid, 5 mg/l Growth is monitored by the increase in turbidity at 600 nm. Cells can be stored in the same medium at 4° C. and remain viable for at least a year, although periodic transfer is recommended.

Large scale (preparative) growth of *P. furiosus* was performed as follows:

Growth medium according to Table 1, was prepared, except that the sulfide was replaced with titanium (III) nitrilotriacetate [final concentration, 30 μM as described in Moench et al., *J. Microbiol. Meth.*, 1:199–202 (1983)] and the elemental sulfur is omitted. The medium was then sparged with Argon (Ar).

A two liter flask was inoculated with two 100 ml cultures. The two liter culture was used as an inoculum for a 20 liter culture. Two 20 liter cultures were used to inoculate a 500 liter culture. The culture was maintained at 88° C., bubbled with Ar (7.5 liters/min) and stirred at about 50 rpm. After about 20 hours ($A_{600}$~0.5) the cells were harvested with a Sharples continuous flow centrifuge at 100 liters/hour. The cells were frozen in liquid N2 immediately after harvesting. The yield of cells is typically 400–600 g wet weight.

It should be noted that *P. furiosus* has a fermentative type of metabolism and produces organic acids, $CO_2$ and $H_2$ as final products. $H_2$ production inhibits growth, so cultures have to be sparged with Ar (or any inert gas) to remove $H_2$. Alternatively, elemental sulfur may be added. In this case, the reductant that would otherwise be used to generate $H_2$ is used to reduce elemental sulfur to $H_2S$. The addition of elemental sulfur is convenient for small scale cultures in glass vessels, but its reduction cannot be used to remove inhibitory $H_2$ in 500 liter stainless steel fermentors because of the corrosive nature of $H_2S$.

2. Purification of Pfu DNA Ligase

A. Lysis of Pfu Cell Paste

Five hundred grams (g) of Pfu cell paste prepared in Example 1 were thawed at room temperature. Two thousand milliliters (ml) of lysis buffer consisting of 50 millimolar (mM) Tris-HCl, pH 8.2, 10 mM beta mercaptoethanol, 1 mM EDTA and 200 microgram/ml (μg/ml) of lysozyme were admixed in a 4:1 volume to mass ration with the thawed cell paste. The admixture was thereafter passed through a French press for two cycles at 2000 psi. All remaining steps were done at 4° C. The cell lysate was then sonicated for 2 minutes at 90% duty, full power at room temperature. Cell debris was then removed by centrifuging for 15 min at 14,000 RPM (or 45 min at 9000 RPM) in a SA600 rotor at room temperature and the supernatant recovered. The supernatant was recovered and dialyzed against Buffer C [50 mM Tris-Cl (pH 8.0), 10% glycerol, 1.0 mM EDTA, 1.0 mM DTT, 0.1% Tween-20, 0.1% NP-40].

B. Column Chromatography of Pfu Cell Lysate

The supernatant prepared above was loaded at 1–2 ml/min on to a one liter fast flow Q-sepharose (2.5×40 centimeter; Pharmacia, Upsalla, Sweden) column at room temperature. The column had been equilibrated in Buffer C. The column containing the cell lysate supernatant was then washed with 2 column volumes (400 ml) of column Buffer C. Elution was done with a linear gradient of 0–0.5M KCl in buffer C in six liters collecting 25 ml fractions. The ligase elutes approximately half way through this gradient (about 0.25M). The column fractions were assayed as described below for ligase activity, peak activity pooled, and dialyzed in buffer C (pH 6.5).

A phospho-cellulose (P11, from Whatman; Clifton, N.J.) column was equilibrated in buffer C. The pooled peak is removed from dialysis and loaded onto the P11 column at 1–2 ml/min. The column was then washed with 2 column volumes of buffer C. Column size for a large scale (500 g starting material) was one liter, and 100 ml for a small scale (18 g starting material). Elution was then carried out with a 0–1.0M KCl gradient in 10 column volumes buffer C. The ligase elutes in a broad band at around 0.5M KCl. After activity and protein gel analysis the ligase peak was pooled and dialyzed in buffer C at pH 6.5. Protein gel analysis was done on a pre-poured Novex (San Diego, Calif.) 4–20% gradient acrylamide gel, and protein was detected with silver stain.

After dialysis the pool from P11 chromatography was then loaded at 4 ml/min onto a 50 ml Pharmacia Hi-load S sepharose column equilibrated in buffer C at pH 6.5. After washing with 2 column volumes the ligase was eluted with a 0–0.5M KCl gradient in buffer C (pH 6.5). The peak ligase fractions are selected after activity and protein gel analysis, pooled, and dialyzed in buffer D. Buffer D contains 10 mM potassium phosphate (pH 6.5), 10% glycerol, 1.0 mM EDTA, 1.0 mM DTT, 0.1% Tween-20, 0.1% NP-40.

A 100 ml dye ligand column (Mimetic Red2 from Affinity Chromatography Ltd; Isle of Man, British Isles) was equilibrated in buffer D. The above dialyzed sample was then loaded onto the column at 1 ml/min followed by a one column volume wash. The Pfu ligase was the only protein that binds the column at this point. The ligase was eluted with a step gradient of 0.1M KCl in buffer D for 1–1.5 column volumes, followed by another step at 0.2M for one volume. Five ml fractions were collected, and each assayed for ligase activity. The ligase eluted during the 0.1M step.

After protein gel and activity assays, the peak activity was pooled and concentrated in Centricon P10 spin concentrators (Amicon; Beverly, Mass.) until an approximate 10 fold concentration was achieved.

The concentrated product was then dialyzed in final dialysis buffer which contains 50 mM Tris-Cl, 50% glycerol, 1 mM EDTA, 1 mM DTT, 0.1% Tween-20, 0.1% NP-40.

The resulting product is referred to as KCl-free purified Pfu DNA ligase. The resultant salt-free Pfu DNA ligase was determined to be about 95% homogeneous by analysis of polyacrylamide gel electrophoresis (PAGE).

3. Nick Sealing Ligation Activity of Pfu DNA Ligase

The collected fractions from Example 2 were separately assayed for Pfu DNA ligase activity in a nick sealing ligation reaction on a synthetic template.

The materials used in the nick sealing ligation reaction assay described below were obtained as follows. T4 Polynucleotide kinase from recombinant *E. coli*, dithiothreitol, urea, acrylamide, bis-acrylamide, ammonium persulfate, TEMED, 10x TBE, and 95% formamide stop dye were obtained from Stratagene Cloning Systems (La Jolla, Calif.). Tth DNA ligase from *Thermus thermophilus* (Tth) was obtained from Abbot Laboratories (Abbot Park, Ill.). *E. coli* T4 DNA ligase was obtained from Stratagene. Adenosine 5'-[gamma-$^{32}$P] triphosphate, triethylammonium salt, was obtained from Amersham Corporation (Arlington Heights, Ill.). Bis-Tris, beta-nicotinamide adenine dinucleotide (NAD), potassium chloride, magnesium chloride, and ammonium chloride were obtained from Sigma Chemical Co. (St Louis, Mo.).

The three oligonucleotide probes used in this reaction were synthesized on an Applied Biosystems (Foster City, Calif.) oligonucleotide synthesizer and purified by PAGE. The oligonucleotides consisted of one 75-mer (A) with the two complementary 35-mers (B, C). Their sequences are as follows (5' to 3') respectively, SEQ ID NOS. 3–5:

| Oligo A: | ATCGCATGGT | CACTCATCGA | AGTCGCTCTG | TCATAGCCCA |
|---|---|---|---|---|
|          | TGCTGGACGT | ACGACGACTA | CTATGTGACT | GCACG |
| Oligo B: | GCAGTCACAT | AGTAGTCGTC | GTACGTCCAG | CATGG |
| Oligo C: | GCTATGACAG | AGCGACTTCG | ATGAGTGACC | ATGCG. |

For the nick sealing ligation reaction assay, 12 pmol of Oligo C was radiolabeled at the 5' end by incubating for 30 minutes at 37° C. in the presence of adenosine 5'(gamma-$^{32}$P] triphosphate and 5 Units of polynucleotide kinase, in a 10 µl volume of 50 mM Tris-HCl (pH 7.5), 7 mM MgCl$_2$, 1 mM dithiothreitol. The polynucleotide kinase was then inactivated by heating at 70° C. for 10 minutes. 1 µl of cell lysate or column eluate was placed in a 500 µl eppendorf tube along with 9 µl reaction buffer and 1 pmol each of the oligonucleotide probes A, B, and 5' radiolabeled C. Nick sealing ligation reaction buffer consisted of 50 mM Bis-Tris pH 6.5, 10 mM MgCl$_2$, 10 mM NH$_4$Cl, 10 mM KCl, 1 mM dithiothreitol and 1 mM NAD. The reaction mixture was then placed in a 55° C. heating block for 15 minutes, then 10 µl 95% formamide stop dye was added to the tube. 10 µl of each sample was loaded on a 1× TBE, 19.7% acrylamide, 0.3% bis-acrylamide, 7M urea gel, 0.4 mm thick, 48 cm×43 cm, with flat wells for loading the samples. Electrophoresis was carried out at 60 watts for 2 hours, then the gel was exposed to Kodak X-OMAT film for 12 hours.

Samples containing nick sealing activity indicative of DNA ligase exhibit the production of a nucleotide fragment formed by the ligation of a fragment corresponding to 5'-A-B-3', and migrate more slowly on the gel than Oligo A or Oligo B alone.

Fractions identified by the assay to contain nick sealing activity were designated as fractions that contained Pfu DNA ligase.

The effects of pH on nick sealing activity of Pfu DNA ligase was analyzed using the above assay except the buffer for pH 5 and 6 was 50 mM Bis-tris, 10 mM MgAc, 10 mM DTT, 0.01 mg/ml BSA, 0.6 mM NAD, 0.1% NP-40, 10 mM NH$_4$Cl, and the buffer for pH's 7, 8 or 9 was the same except that 50 mM EPPS was substituted for Bis-tris. Ligation was conducted using 5 units of enzyme at 55° C. for 12 min when using Pfu or Tth DNA ligases, and at 37° C. for T4 DNA ligase.

The results of the pH-dependence study are shown in FIG. 1. The data show that Pfu DNA ligase has a broader pH activity range (pH 6–8) than Tth (pH 8–9) or T4 (pH 8–9) DNA ligases. The broader pH range provides for a greater diversity of hybridization conditions under which the enzyme may be utilized.

4. Blunt End Ligation Activity of Pfu DNA Ligase

The materials used in the blunt end ligation assay are identical to those used in Example 3, with the exception of the two oligonucleotide probes. These two oligonucleotide probes are complementary 25-mers, and their sequences are as follows (5' to 3') "respectively, SEQ NOS. 6–7":

Oligo D: AGCAACGACT GTTTGCCCGC CAGTT

Oligo E: AACTGGCGGG CAAACAGTCG TTGCT.

Both oligos were radiolabeled on their 5' ends by incubating for 30 minutes at 37° C. in the presence of adenosine 5'(gamma-$^{32}$P) triphosphate and 5 Units of polynucleotide kinase, in a 10 µl volume of 50 mM Tris-HCl (pH 7.5), 7 mM MgCl$_2$, 1 mM dithiothreitol. The polynucleotide kinase was then inactivated by heating at 70° C. for 10 minutes. 1 µl of cell lysate or column eluate was placed in a 500 µl eppendorf tube along with 9 µl reaction buffer and 1 pmol each of the radiolabeled oligonucleotide probes D and F. The reaction mixture was then placed in a 55° C. heating block for 1 hour, then 10 µl 95% formamide stop dye was added to the tube. 10 µl of each sample was then analyzed on an acrylamide gel as described in Example 3.

The results of the blunt end ligation assay show that in a single-cycle ligation reaction, T4 DNA ligase ligates a significant amount of the substrate oligonucleotides, but neither the Tth or Pfu DNA ligase exhibit detectable blunt end ligation.

5. Ligase Chain Reaction Activity of Pfu DNA Ligase

A ligase chain reaction (LCR) assay was conducted using reagents identical to those in Example 3, with the exception of the oligonucleotide probes and the DNA templates used. The DNA templates was a plasmid construct of pBluescript vector and the lac I gene. The wild type template contains a normal lac I sequence, and the 2B89 template contains a known T to C transition at site 191. The four oligonucleotide probes for these plasmid templates consist of two sets of two oligos each. The first set of oligonucleotides, Oligo A and Oligo B (described below), are continuous to each other and complementary to one strand of the target. The second set of oligonucleotides, Oligo C and Oligo D (described below), are complementary to the first set, and therefore occupy adjacent sites on the second strand of the target DNA. All four oligonucleotide probes were synthesized as described in Example 3. The sequences of the oligonucleotide probes are as follows: (5' to 3') "respectively, SEQ ID NOS 8–11"

Oligo A: GTTGTGCCAC GCGGTTGGGA ATGTA

Oligo B: AGCAACGACT GTTTGCCCGC CAGTT

Oligo C: TACATTCCCA ACCGCGTGGC ACAA

Oligo D: CAACTGGCGG GCAAACAGTC GTTGCT.

12 pmol of oligonucleotide probes Oligo A and Oligo D were radiolabeled at their 5' ends by incubating for 30 minutes at 37° C. in the presence of adenosine 5'(gamma-$^{32}$P) triphosphate and 5 Units of polynucleotide kinase, in a 10 µl volume of 50 mM Tris-HCl (pH 7.5), 7 mM MgCl$_2$, 1 mM dithiothreitol. The polynucleotide kinase was then inactivated by heating at 70° C. for 10 minutes. 1 pmol of each of the radiolabeled probes A and D and 1 pmol each of the probes Oligo B and Oligo C were added to a 500 µl eppendorf tube, along with 5 pmol of plasmid template WT or 2B89, or no template. Each tube contained a total volume of 50 µl of reaction buffer, consisting of 50 mM bis-Tris pH 6.5, 10 mM MgCl$_2$, 10 mM NH$_4$Cl, 10 mM KCl, 1 mM dithiothreitol and 1 mM NAD. A 50 µl volume of mineral oil was overlaid into each tube, and the tubes were heated to 100° C. for 3 minutes, then cooled to 85° C. for 1 minute, then kept at 55° C. while 3000 Units of DNA ligase enzyme was added. The reaction tubes were then placed in a DNA thermocycler (RoboCycler, Stratagene) and cycled between 85° C. and 50° C. 30 times, for 1 minute at each temperature. 10 µl of each reaction were diluted 1:1 with 10 µl95% formamide stop dye. 10 µl of each diluted sample was the analyzed on an acrylamide gel as described in Example 3.

The results using a plasmid template show that Tth DNA ligase contains an appreciable amount of ligation when using a single base mismatched template (2B89), whereas Pfu DNA ligase produced no detectable ligation on the mismatched template, whereas both DNA ligases produced a ligation product when using the complementary template (wild type).

6. Cofactor Dependence of Pfu DNA Ligase Activity

Pfu DNA ligase was assayed using the reagents described in Example 3 with the following exceptions. Five thousand units of either Tth DNA ligase or Pfu DNA ligase was admixed in a 500 ul eppendorf tube with a 10 ul volume of 50 mM Bis-tris pH 6.5, 10 mM $MgCL_2$, 10 mM $NH_4KCl$, 10 mM KKCl, 1 mM DTT, 10 uCi of either (gamma-$^{32}$P) rATP or (Adenylate-$^{32}$P)NAD (both obtained from Dupont-NEN, Boston, Mass.) was added to each tube, and the admixtures were incubated at 70° C. for 30 min. The samples were then loaded onto a 12% acrylamide Tris-glycine gel (Novex, Encinitas, Calif.) and electrophoresed at 40 mA for 90 min. The PAGE gels were then placed on Kodak X-OMAT film for 30 min.

The results show differential migration on the gel when the radioactive cofactor binds to the DNA ligase protein and therefor migrates on the gel as a protein instead of a small macromolecule. NAD bound to both Pfu and Tth DNA ligase, whereas only rATP bound to Pfu DNA ligase.

7. Thermoactivity of Pfu DNA Ligase

The enzyme activity of Pfu DNA ligase and Tth DNA ligase was compared at different temperatures using the nick-sealing assay described in Example 3. A reaction mixture containing buffer and radiolabeled DNA substrate as described in Example 3 was added to a 500 ul eppendorf tube, overlayed with mineral oil, and the placed on a heating block and maintained a one of various temperatures. After reaching temperature equilibrium, 10 units of Tth or Pfu DNA ligase was added to the tube, and the reaction admixture was maintained for 30 min. Thereafter, 10 ul of formamide stop dye was added to each tube, the samples were heated to 95° C., and analyzed on a 20 % acrylamide, 7M urea, 1×TBE gel by electrophoresis at 60 watts for 2 hours. The electrophoresed gel was exposed to Kodak X-OMAT film for 10 hours.

Figure 2:
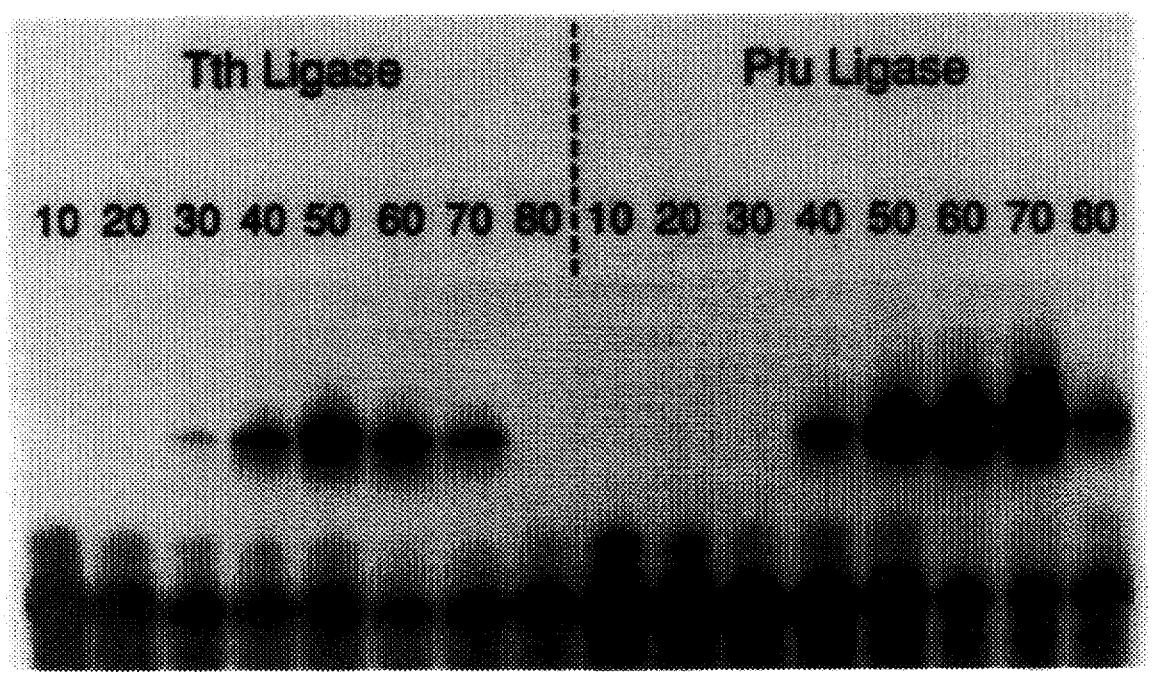
FIG. 2 illustrates an PAGE analysis of a nick sealing ligation activity assay that measures the temperature-dependence of Pfu DNA ligase activity as described in Example 7. Lanes 1–8 contain Tth DNA ligase assayed at the indicated temperatures of 10 to 80 degrees C. Lanes 9–16 contain Pfu DNA ligase assayed at the indicated temperatures of 10 to 80 degrees C.

The results, shown in FIG. 2, shows that Tth DNA ligase exhibited an activity range of 20° C.–70° C., with an optimum of about 50° C., whereas Pfu DNA ligase exhibited an activity range of about 30° C.–80° C., with an optimum of about 70° C. Thus, Pfu DNA ligase is active at a higher range of temperatures than Tth DNA ligase, providing the benefit of hybridization under more stringent conditions, allowing oligonucleotides to be designed with a higher specificity or for higher stringency.

8. Thermostability of Pfu DNA Ligase

The enzyme stability of Pfu DNA ligase and Tth DNA ligase was compared at different temperatures using the nick-sealing assay described in Example 3. A reaction mixture containing buffer and 10 units of DNA ligase as described in Example 3, but lacking DNA substrate, was added to a 500 ul eppendorf tube, overlayed with mineral oil, and the placed on a heating block and maintained a one of various temperatures for 30 min. Thereafter, 1 picomole (pmole) of DNA substrate as described in Example 3 was added to each tube, and the reaction admixture was maintained at 55° C. for 30 min. Thereafter, 10 ul of formamide stop dye was added to each tube, the samples were heated to 95° C., and analyzed on a 20% acrylamide, 7M urea, 1× TBE gel by electrophoresis at 60 watts for 2 hours. The electrophoresed gel was exposed to Kodak X-OMAT film for 10 hours.

Figure 3:
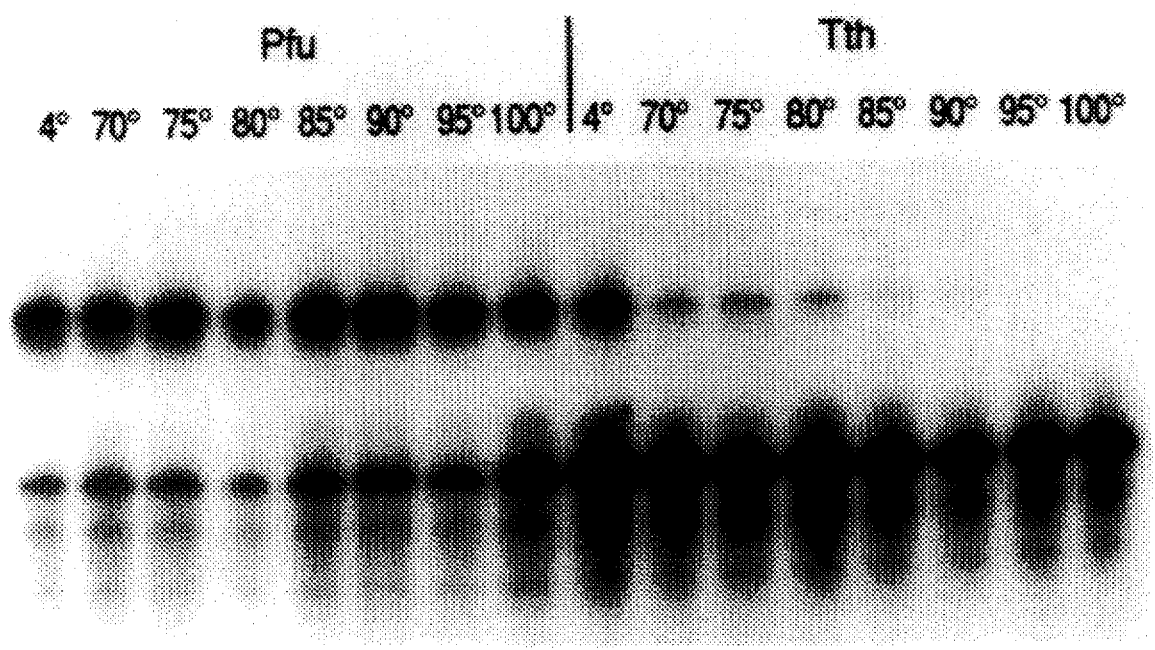
FIG. 3 illustrates an PAGE analysis of a nick sealing ligation activity assay that measures the temperature stability of Pfu DNA ligase after a 30 minute preincubation for the time periods shown as described in Example 8. The left eight lanes show the stability of Pfu DNA ligase from 4° C. to 100° C., and the right eight lanes show the stability of Tth DNA ligase from 4° C. to 100° C.

The results, shown in FIG. 3, shows that Tth DNA ligase maintained DNA ligase activity over a temperature range of 4° C.–65° C., whereas Pfu DNA ligase maintained DNA ligase activity over a temperature range of 4° C.–100° C. Thus, Pfu DNA ligase is thermostable over a significantly greater range of range of temperatures than Tth DNA ligase, and particularly, is thermostable at much higher temperatures than Tth DNA ligase.

The increased thermostability of Pfu DNA ligase provides a unique advantage over Tth DNA ligase at the initial double-stranded (ds) template melting step during LCR. Whereas LCR using Tth DNA ligase must be conducted by first melting the ds DNA at high temperature prior to adding the Tth DNA ligase, necessitating the addition of Tth DNA ligase after the first cycle, LCR using Pfu can be conducted by adding the enzyme prior to melting, and without stopping the LCR reaction after the first cycle to add enzyme. In addition, due to the increased temperature stability, LCR can be conducted with less enzyme because it is less susceptible to loss of activity during the temperature cycling phase of LCR.

9. Molecular Weight Determination

The molecular weight of the purified Pfu DNA ligase prepared in Example 2D was determined by SDS-PAGE under denaturing conditions according to the method of Laemmli et al., *J. Mol. Biol.*, 80:575–599 (1973). Five thousand units of Pfu DNA ligase and Tth DNA ligase were reduced in DTT, loaded onto a 12% acrylamide Tris-glycine SDS-polyacrylamide gel (Novex, Encinitas, Calif.) and electrophoresed in a running buffer containing 1% SDS, 2.4 mM Tris, and 18 mM glycine at 35 milliamps (mA) for 90 min. Five ul of low molecular weight SDS gel markers (Biorad) were also run on the gel, and contain bovine serum albumin (66,200 daltons) and hen egg white ovalbumin (45,000 daltons). The gel was then stained with Coomassie Brilliant Blue R-250 (Sigma) and photographed.

Figure 4:
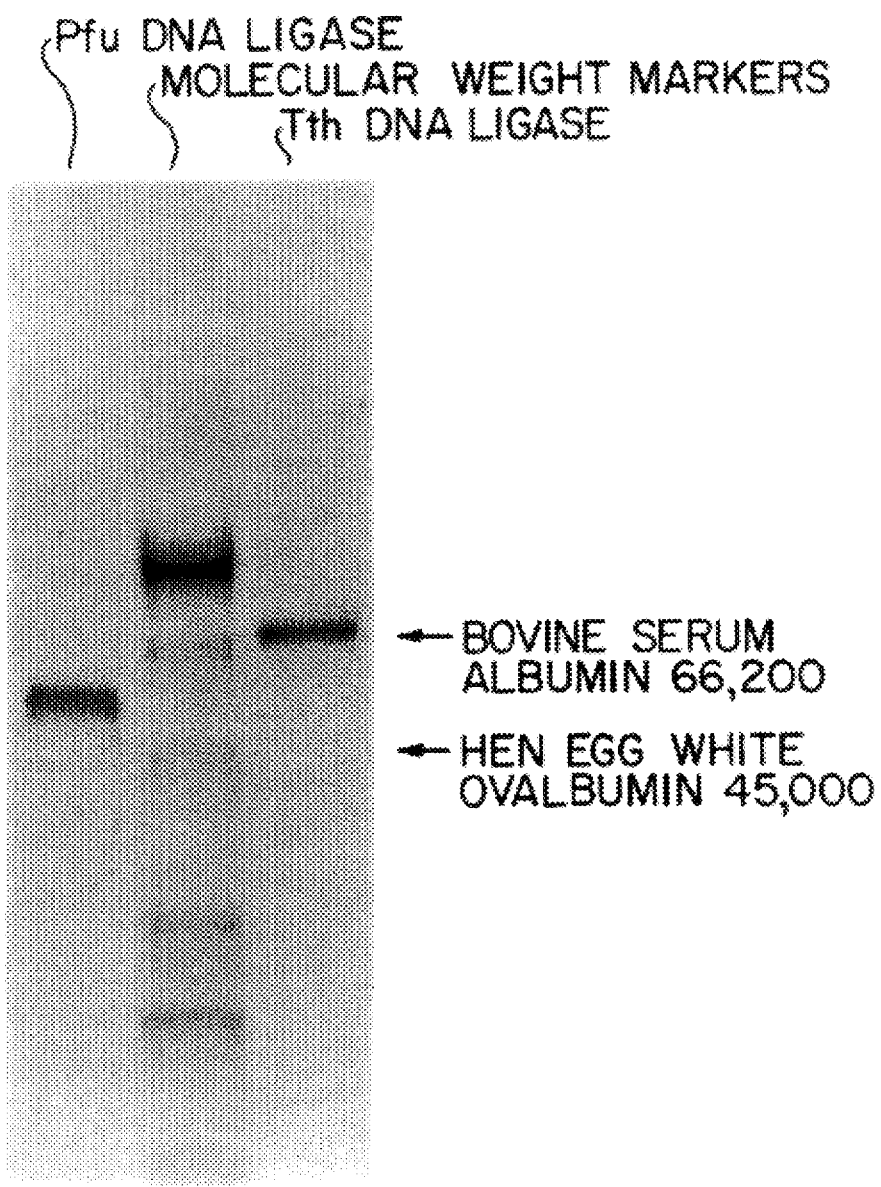
FIG. 4 illustrates a molecular weight determination of Pfu DNA ligase compared to standard proteins by SDS-PAGE analysis (12% gel, under reducing conditions) as described in Example 9. Molecular weight standards are electrophoresed in the center lane. The molecular weights of the protein standards hen egg white ovalbumin (45,000 daltons) and bovine serum albumin (66,200 daltons) are indicated by arrows. In the left lane, Pfu DNA ligase exhibits a molecular weight of about 55,000 to 65,000 daltons, whereas in the right lane Tth DNA ligase exhibits a molecular weight of about 69,000 to 70,000 daltons.

The results of that analysis, shown in FIG. 4, indicate that Pfu DNA ligase migrates faster than bovine serum albumin (66,200 daltons) and Tth DNA ligase (78,000 daltons) but slower than hen egg white ovalbumin (45,000 daltons). Because of its migration in the SDS-PAGE gel relative to the marker proteins, Pfu DNA ligase was assigned a relative molecular weight of about 55,000 to 65,000 daltons, and more preferably is about 58,000 to 64,000 daltons.

10. Cloning the Gene that Encodes Pyrococcus furiosus (Pfu) DNA Ligase

The gene encoding thermostable DNA ligase has been cloned from the hyperthermophilic marine archaebacterium, *Pyrococcus furiosus* (Pfu).

Amino terminal protein microsequencing was performed by the Wistar Institute (PA) on 10 picomoles (pmol) of homogeneous native Pfu DNA ligase prepared as described in Example 3. The sequence of the 50 N-terminal amino acid residues thereby obtained were later shown to correspond exactly with the 50 deduced residues shown in SEQ ID NO 1 from residue 1 to residue 50.

Based on the 50 residue sequence obtained, and the limited knowledge of codon usage in Pyrococcus, a series of PCR primers were designed to amplify the N-terminus of the gene. This type of primer design is referred to as TM-PCR (tolerated mismatch PCR). The theory behind TM-PCR is that a thymidine nucleotide paired with any other nucleotide (A,C,G,T) has a low energy of destabilization and therefore is a tolerated mismatch which will allow the oligonucleotide to hybridize efficiently to the template DNA. In order for the primer to serve as an effective substrate for a DNA polymerase, the 3' end of the primer must possess near perfect complementarity to the template. Thus, primers were designed such that the eight 3' terminal nucleotides matched the predicted nucleotide sequence. This TM-PCR primer design required four primers to be synthesized for each end of the PCR fragment. Thus, one of the four primers from each set was perfectly matched at the 3' eight nucleotide (nt) positions within the template DNA. All sixteen possible primer pairs were used to amplify an 92 bp expected product from genomic *Pyrococcus furiosus* DNA. One set of four primers were seventeen nt and the other set were twenty nts. all of which contained thymidine at every degenerate position 5' to the eight 3' terminal nucleotides. The use of thymidine mismatched primers is preferable to degenerate primers because after the first PCR cycle, every PCR primer will be perfectly matched to the newly synthesized templates. In contrast, when amplifying with degenerate primers, throughout PCR there is always is a competition for the template binding site between each oligonucleotide within the degenerate primer pool. PCR was performed essentially according to the GeneAmp kit, except that Pfu DNA polymerase (Stratagene Inc, La Jolla, Calif.) was substituted for Taq polymerase. *Pyrococcus furiosus* genomic DNA was prepared with minor modifications of the method described by Gross-Bellard et al (1973). Of the sixteen PCR primer sets evaluated, twelve yielded only the expected 92 bp product. The 55 nt sequence spanning the PCR primers was deduced by direct cycle sequencing of the amplified products. The PCR fragment was found to contain 100% sequence homology with the known amino acid sequence. The success of this approach was at least partially due to the 62% AT content of the *Pyrococcus furiosus* genome. A 25 base synthetic oligonucleotide probe corresponding to the reverse complement of this sequence was then constructed and used to directly cycle-sequence genomic *Pyrococcus furiosus* DNA and obtain the actual start site along with 100 nts upstream of the initiation codon.

A set of two nested primers spanning the region upstream of the initiation codon were used in conjunction with the vectorette strategy (described below) to obtain about 500 nt and about 2100 nt genomic walks downstream of the initiation codon of Pfu DNA ligase. Based on the predicted molecular weight of about 55 to 60kD for Pfu DNA ligase, calculated from SDS-PAGE estimations, the entire coding sequence was predicted to reside in the 2100 nt vectorette fragment. Following sequence determination of the 3' end of the 2 kB fragment (using the vectorette primer as a sequencing primer), primers were constructed which would amplify the entire ligase gene. The unique restriction sites, BglII and SalI. were introduced into the 5' ends of the PCR primers to facilitate cloning of the gene into pBluescript vector (Stratagene). After 20 cycles of PCR amplification with Pfu polymerase, the PCR products were double digested with BglII and SalI, the enzymes removed with StrataClean resin (Stratagene), the digested PCR product was isolated free of linker fragments by concentration in a Centricon 100 ultra-filtration unit (Amicon) and ligated into Bam HI/SalI digested pBluescript vector. Following transformation into XL1Blue competent cells (Stratagene), the clones were screened for thermostable ligase activity as described in Example 3. Three of the ten clones assayed possessed thermostable DNA ligase activity. A six liter fermentation of *E. coli* harboring the Pfu ligase gene was next performed and the recombinant enzyme purified as described in Example 11.

In a preferred embodiment, the above primers are also designed to introduce into the resulting cloned gene nucleotides coding for the first several amino acid residues to reflect the preferred codon usage for *E. coli*, thereby facilitating efficient expression in *E. coli*.

Vectorette Cloning

The general steps involved in the vectorette genomic gene walking technique are described by Arnold et al., *PCR Methods and Applications*, 1:39–42 (1991). In summary, there are 4 basic steps: (1) digestion of the target DNA with a suitable restriction enzyme (using EcoRI, BamHI, KpnI and HindIII in the present cloning procedure); (2) ligation of suitable synthetic double-stranded oligonucleotide linkers to the digested DNA; the linkers are constructed so that they possess the appropriate restriction overhang onto their 5' ends to allow ligation to the digested target DNA and the upper strand oligonucleotide contains 15 to 20 more 3' terminal nucleotides than the lower strand; (3) 30 cycles of linear amplification using a known target sequence primer from the 5' end of the know sequence; and (4) 30 cycles of PCR using a primer nested inside the primer used in step (3) and a primer designed to be complementary to the 20 3' terminal nucleotides of upper strand of the linker.

The vectorette cloning technique, when used in conjunction with N-terminal sequence analysis, TM-PCR and direct genomic sequencing, provides a method to clone Archaebacterium pfu DNA ligase genes without the need for library construction. For example, the entire coding sequence of *Pyroccocus furiosus* DNA ligase was obtained on one 2.1 kilobase (kB) HindIII vectorette fragment using the procedure. Following restriction mapping of vectorette fragment, PCR primers with unique restriction enzyme sites were designed to amplify to entire 2.1 kB fragment from genomic DNA and allow cloning the Pfu ligase gene directly into pBluescript vector.

The resulting plasmid, designated pEM1, contains the complete 2.1 kB DNA fragment encoding Pfu DNA ligase flanked at the fragment's termini by BamHI and SalI. When the BamHI to SalI fragment is cloned into pBluescript vector, a nucleotide sequence defining a fusion protein open reading frame is formed, such that the expressed recombinant Pfu DNA ligase is a fusion protein comprising both beta-galactosidase and Pfu DNA ligase.

The sequence of the cloned 2.1 kB was determined by standard nucleic acid sequencing methods, and a majority of the 2.1 kB fragment nucleotide sequence is shown in SEQ ID NO 2. The sequence determined contains 2185 nucleotide bases, and has a number of base residues that were not confirmed by producing second-strand sequence data, and therefore, the actual sequence may very upon the preparation of confirming nucleotide sequence data.

The deduced amino acid sequence of Pfu DNA ligase is shown in SEQ ID NO 1 and exhibits a substantially higher degree of homology with human DNA ligase I (ca. 22% identity) than Tth ligase (ca 10% identity), or *E. coli* DNA ligase (ca 5.3% identity).

11. Purification of Recombinant Pfu DNA Ligase

Recombinant Pfu ligase was purified from *E. coli* containing the plasmid pEM1 described in Example 10. Cultures of *E. coli*/pEM1 were prepared as before, and 20 grams of the cultured cells were isolated, admixed in 80 ml lysis buffer (prepared as in Example 2A) and sonicated 3 times for 2 minutes each at full power. The resulting lysate was centrifuged for 30 minutes at 9000 rpm. The supernatant from the centrifugation was isolated and then brought to 75° C. in a water bath and incubated for 10 minutes to form a heat-denatured solution. The heat-denatured solution was then centrifuged as above and the resulting supernatant was isolated and then loaded onto a Q-sepharose column equilibrated in buffer C at pH 8 as described in Example 2B. The column was washed with 2 column volumes of buffer C and then eluted with an 8 column volume gradient of 0–0.5M KCl in buffer C as before, collecting gradient eluant fractions. A nick sealing ligation activity assay was performed on each fraction and peak activity fractions were pooled and dialyzed in buffer C at pH 6.

Following dialysis, the dialysate was loaded on a PlI column equilibrated at pH 6 as described in Example 2B. The column was washed with 2 column volumes and eluted with a 0–1.0M KCl gradient in buffer C. Peak activity fractions were collected, assayed and active fractions were pooled and concentrated 4–5 fold in a Centricon P10 spin concentrator. The concentrated pool was then dialyzed against final dialysis buffer to form purified recombinant Pfu DNA ligase.

DNA ligase activity of a preparation of Pfu DNA ligase was determined by comparison to commercial sources of Tth DNA ligase. Using the nick sealing ligation assay described in Example 3, dilutions of Tth DNA ligase in reaction buffer from 0.1 to 100 units per assay reaction were run and analyzed on PAGE as described to produce a variety of ligated reaction products whose intensity by PAGE analysis varied depending upon the amount of ligase added. A similar dilution series was prepared for Pfu DNA ligase, and reacted in a parallel nick sealing ligation assay, and the results analyzed by PAGE. Based on relative band intensity upon comparison to the dilutions of Tth DNA ligase having a known DNA ligase activity, units of activity were assigned to the Pfu DNA ligase preparation produced above. Recombinant and native Pfu DNA ligase assayed in this manner for DNA ligase activity consistently yielded compositions of pure enzyme having 500 to 5000 units per microliter (ul), when compared to the activity of Tth DNA ligase.

12. Ligase Chain Reaction With Recombinant Pfu DNA Ligase

The materials used in this LCR reaction are identical to those used in Example 3, with the exception of the Pfu DNA ligase enzyme, which is the recombinant enzyme produced as described in Example 11, and the LCR templates and oligonucleotide probes. The templates consist of two complementary 36-mer synthetic oligonucleotides, and the probes consist of 18-mer oligonucleotide probes. The two templates have sequences as follows (5' to 3') "respectively, SEQ ID NO 12–17":

Template J:GACTCCAAGG TTGTGTCCAA TGTGGTCACC TTCGCT

Template I:AGCGAAGGTG ACCACATTGG ACACAACCTT GGAGTC

Oligo A:GACTCCAAGG TTGTGTCC

Oligo B:AATGTGGTCA CCTTCGCT

Oligo C:AGCGAAGGTG ACCACATT

Oligo D:GGACACAACC TTGGAGTC 12 pmol of oligonucleotide probes Oligo B and Oligo C were radiolabeled at their 5' ends by incubating for 30 minutes at 37° C. in the presence of adenosine 5'(-$^{32}$P] triphosphate and 5 Units of polynucleotide kinase, in a 10 µl volume of 50 mM Tris-HCl (pH 7.5), 7 mM MgCl$_2$, 1 mM dithiothreitol. The polynucleotide kinase was then inactivated by heating at 70° C. for 10 minutes. 1 pmol of each of the radiolabeled probes Oligo B and Oligo C, and 1 pmol each of the probes Oligo A and Oligo D, were added to a 500 µl eppendorf tube, along with 0.01 nanogram (ng), 0.1 ng, 1 ng, or 10 ng of each of the synthetic templates I and J, or no template to form a ligation chain reaction admixture. Each tube contained a total volume of 50 µl of reaction buffer, consisting of 50 mM bis-Tris pH 6.5, 10 mM MgCl$_2$, 10 mM NH4KCl, 10 mM KKCl, 1 mM dithiothreitol, and 1 mM NAD. A 50 µl volume of mineral oil was overlaid into each tube, and the tubes were heated to 100° C. for 3 minutes, then cooled to 85° C. for 1 minute, then kept at 55° C. while 3000 Units of recombinant Pfu DNA ligase enzyme (prepared as described in Example 11), or commercially prepared Tth DNA ligase, were added. The reaction tubes were then placed in a DNA thermocycler (RoboCycler, Stratagene) and cycled between 85° C. and 50° C. 30 times, for 1 minute at each temperature. 10 µl of each reaction were diluted 1:1 with 10 µl 95% formamide stop dye. 10 µl of each diluted sample was loaded on a 1× TBE, 19.7% acrylamide, 0.3% bis-acrylamide, 7M urea gel, 0.4 mm thick, 48 cm×43 cm, with flat wells for loading the samples. Electrophoresis was carried out at 60 watts for 2 hours, then the gel was exposed to Kodak X-OMAT film for 12 hours.

Figure 5:
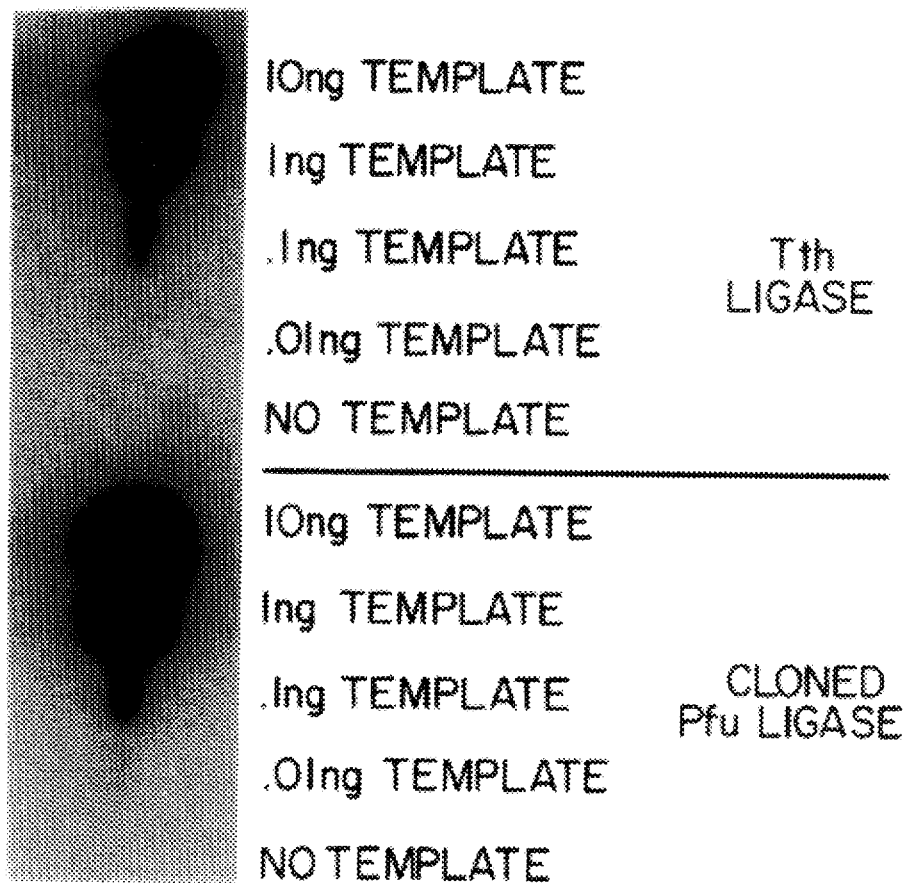
FIG. 5 illustrate an LCR reaction using a synthetic template according to Example 12, and compares the activity of both Tth DNA ligase and Pfu DNA polymerase. Lanes 1–5 illustrate the ligation reaction product formed using 3000 units of Tth DNA ligase, and lanes 6–10 illustrate the ligation reaction product formed using 3000 units of recombinant (cloned) Pfu DNA ligase. The amounts of template added to the ligation reaction are 10 ng (lanes 1 and 6), 1 ng (lanes 2 and 7), 0.1 ng (lanes 3 and 8), 0.01 ng (lanes 4 and 9), and no template (lanes 5 and 10).

The results are shown in FIG. 5, and illustrate that both Tth DNA ligase and Pfu DNA ligase perform well in LCR after multiple cycles forming a single LCR DNA fragment without appreciable blunt-end ligation or background reaction products.

To demonstrate the ability of Pfu DNA ligase to perform well in LCR without a "pre-melting" step, the same reaction as above was run, except that the reaction tubes were heated to 95° C. for 10 minutes after the DNA ligase was added, and before the cycling, to emulate a genomic DNA melting step. Thereafter the reaction tubes were cycled as before, and the reaction products were analyzed on PAGE as before. The results showed that the expected LCR product was formed when Pfu DNA ligase was used, but no detectable LCR product was detected when using the Tth DNA ligase, indicating that the Tth DNA ligase is not heat stable when exposed to temperatures required to separate the strands of double-stranded genomic DNA.

The foregoing written specification is considered to be sufficient to enable one skilled in the art to practice the invention. The present invention is not to be limited in scope by the biological material deposited, since the deposited embodiment is intended as a single illustration of on aspect of the invention and any biological materials that are functionally equivalent are within the scope of this invention. The deposit of materials therein does not constitute an admission that the written description herein contained is inadequate to enable the practice of any aspect of the invention, including the best mode thereof, nor are the deposits to be construed as limiting the scope of the claims to the specific illustrations that they represent. Indeed, various modifications of the invention in addition to those shown and described herein will become apparent to those skilled in the art from the foregoing description and fall within the scope of the appended claims.

What is claimed is:

1. A purified thermostable DNA ligase from *Pyrococcus furiosus* having the amino acid sequence of SEQ ID NO: 1 which substantially retains activity when subjected to temperatures of from about 85° C. to about 100° C.

2. The ligase of claim 1 that is isolated from a recombinant organism transformed with a vector that codes for the expression of said DNA ligase.

3. A ligase according to claim 1, wherein the ligase is encoded by plasmid pEM1 (ATCC Deposit No. 75259).

* * * * *

UNITED STATES PATENT AND TRADEMARK OFFICE
CERTIFICATE OF CORRECTION

PATENT NO.   : 5,700,672
DATED        : December 23, 1997
INVENTOR(S)  : Mathur et al.

It is certified that error appears in the above-indentified patent and that said Letters Patent is hereby corrected as shown below:

In the title, replace "FURIOUSUS" with --FURIOSUS--.

Column 1, line 2, replace "FURIOUSUS" with -- FURIOSUS--.

Signed and Sealed this

Nineteenth Day of May, 1998

Attest:

BRUCE LEHMAN

Attesting Officer        Commissioner of Patents and Trademarks

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 561 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Pyrococcus Furiosus
        ( C ) INDIVIDUAL ISOLATE: DSM #3638
        ( G ) CELL TYPE: unicellular organism ( v i i ) IMMEDIATE SOURCE:
        ( A ) LIBRARY:Pyroccus Furiosus Genomic DNA
        ( B ) CLONE:pEM1

( x i ) SEQUENCE DESCRIPTION: SEQ ID NO:1:

```
Met Arg Tyr Leu Glu Leu Ala Gln Leu Tyr Gln Lys Leu Glu Lys
 1               5                  10                  15

Thr Thr Met Lys Leu Ile Lys Thr Arg Leu Val Ala Asp Phe Leu
                20                  25                  30

Lys Lys Val Pro Asp Asp His Leu Glu Phe Ile Pro Tyr Leu Ile
                35                  40                  45

Leu Gly Glu Val Phe Pro Glu Trp Asp Glu Arg Glu Leu Gly Val
                50                  55                  60

Gly Glu Lys Leu Leu Ile Lys Ala Val Ala Met Ala Thr Gly Ile
                65                  70                  75

Asp Ala Lys Glu Ile Glu Glu Ser Val Lys Asp Thr Gly Asp Leu
                80                  85                  90

Gly Glu Ser Ile Ala Leu Ala Val Lys Lys Lys Gln Lys Ser
                95                  100                 105

Phe Phe Ser Gln Pro Leu Thr Ile Lys Arg Val Tyr Gln Thr Leu
                110                 115                 120

Val Lys Val Ala Glu Thr Thr Gly Glu Gly Ser Gln Asp Lys Lys
                125                 130                 135

Val Lys Tyr Leu Ala Asp Leu Phe Met Asp Ala Glu Pro Leu Glu
                140                 145                 150

Ala Lys Tyr Leu Ala Arg Thr Ile Leu Gly Thr Met Arg Thr Gly
                155                 160                 165

Val Ala Glu Gly Leu Leu Arg Asp Ala Ile Ala Met Ala Phe His
                170                 175                 180

Val Lys Val Glu Leu Val Glu Arg Ala Tyr Met Leu Thr Ser Asp
                185                 190                 195

Phe Gly Tyr Val Ala Lys Ile Ala Lys Leu Glu Gly Asn Glu Gly
                200                 205                 210

Leu Ala Lys Val Gln Val Gln Leu Gly Lys Pro Ile Lys Pro Met
                215                 220                 225

Leu Ala Gln Gln Ala Ala Ser Ile Arg Asp Ala Leu Leu Glu Met
                230                 235                 240

Gly Gly Glu Ala Glu Phe Glu Ile Lys Tyr Asp Gly Ala Arg Val
                245                 250                 255

Gln Val His Lys Asp Gly Ser Lys Ile Ile Val Tyr Ser Arg Arg
```

-continued

|     |     |     |     |     |     |     |     | 260 |     |     |     | 265 |     |     |     | 270 |
| --- | --- | --- | --- | --- | --- | --- | --- | --- | --- | --- | --- | --- | --- | --- | --- | --- |
| Leu | Glu | Asn | Val | Thr | Arg | Ala | Ile | Pro | Glu | Ile | Val | Glu | Ala | Leu |
|     |     |     |     | 275 |     |     |     | 280 |     |     |     |     |     | 285 |
| Lys | Glu | Ala | Ile | Ile | Pro | Glu | Lys | Ala | Ile | Val | Glu | Gly | Glu | Leu |
|     |     |     |     | 290 |     |     |     | 395 |     |     |     |     |     | 300 |
| Val | Ala | Ile | Gly | Glu | Asn | Gly | Arg | Pro | Leu | Pro | Phe | Gln | Tyr | Val |
|     |     |     |     | 305 |     |     |     | 310 |     |     |     |     |     | 315 |
| Leu | Arg | Arg | Phe | Arg | Arg | Lys | His | Asn | Ile | Glu | Glu | Met | Met | Glu |
|     |     |     |     | 320 |     |     |     | 325 |     |     |     |     |     | 330 |
| Lys | Ile | Pro | Leu | Glu | Leu | Asn | Leu | Phe | Asp | Val | Leu | Tyr | Val | Asp |
|     |     |     |     | 335 |     |     |     | 340 |     |     |     |     |     | 345 |
| Gly | Gln | Ser | Leu | Ile | Asp | Thr | Lys | Phe | Ile | Asp | Arg | Arg | Arg | Thr |
|     |     |     |     | 350 |     |     |     | 355 |     |     |     |     |     | 360 |
| Leu | Glu | Glu | Ile | Ile | Lys | Gln | Asn | Glu | Lys | Ile | Lys | Val | Ala | Glu |
|     |     |     |     | 365 |     |     |     | 370 |     |     |     |     |     | 375 |
| Asn | Leu | Ile | Thr | Lys | Lys | Val | Glu | Glu | Ala | Glu | Ala | Phe | Tyr | Lys |
|     |     |     |     | 380 |     |     |     | 385 |     |     |     |     |     | 390 |
| Arg | Ala | Leu | Glu | Met | Gly | His | Glu | Gly | Leu | Met | Ala | Lys | Arg | Leu |
|     |     |     |     | 395 |     |     |     | 400 |     |     |     |     |     | 405 |
| Asp | Ala | Val | Tyr | Glu | Pro | Gly | Asn | Arg | Gly | Lys | Lys | Trp | Leu | Lys |
|     |     |     |     | 410 |     |     |     | 415 |     |     |     |     |     | 420 |
| Ile | Lys | Pro | Thr | Met | Glu | Asn | Leu | Asp | Leu | Val | Ile | Ile | Gly | Ala |
|     |     |     |     | 425 |     |     |     | 430 |     |     |     |     |     | 435 |
| Glu | Trp | Gly | Glu | Gly | Arg | Arg | Ala | His | Leu | Phe | Gly | Ser | Phe | Ile |
|     |     |     |     | 440 |     |     |     | 445 |     |     |     |     |     | 450 |
| Leu | Gly | Ala | Tyr | Asp | Pro | Glu | Thr | Gly | Glu | Phe | Leu | Glu | Val | Gly |
|     |     |     |     | 455 |     |     |     | 460 |     |     |     |     |     | 465 |
| Lys | Val | Gly | Ser | Gly | Phe | Thr | Asp | Asp | Leu | Val | Glu | Phe | Thr |
|     |     |     |     | 470 |     |     |     | 475 |     |     |     |     |     | 480 |
| Lys | Met | Leu | Lys | Pro | Leu | Ile | Ile | Lys | Glu | Glu | Gly | Lys | Arg | Val |
|     |     |     |     | 485 |     |     |     | 490 |     |     |     |     |     | 495 |
| Trp | Leu | Gln | Pro | Lys | Val | Val | Ile | Glu | Val | Thr | Tyr | Gln | Glu | Ile |
|     |     |     |     | 500 |     |     |     | 505 |     |     |     |     |     | 510 |
| Gln | Lys | Ser | Pro | Lys | Tyr | Arg | Ser | Gly | Phe | Ala | Leu | Arg | Phe | Pro |
|     |     |     |     | 515 |     |     |     | 520 |     |     |     |     |     | 525 |
| Arg | Phe | Val | Ala | Leu | Arg | Asp | Asp | Lys | Gly | Pro | Glu | Asp | Ala | Asp |
|     |     |     |     | 530 |     |     |     | 535 |     |     |     |     |     | 540 |
| Thr | Ile | Glu | Arg | Ile | Ala | Gln | Leu | Tyr | Glu | Leu | Gln | Glu | Lys | Met |
|     |     |     |     | 545 |     |     |     | 550 |     |     |     |     |     | 555 |
| Lys | Gly | Lys | Val | Glu | Ser |
|     |     |     |     | 560 |

( 2 ) INFORMATION FOR SEQ ID NO:2:

( i ) SEQUENCE CHARACTERISTICS:
        ( A ) LENGTH: 2363 base pairs
        ( B ) TYPE: nucleic acid
        ( C ) STRANDEDNESS: double
        ( D ) TOPOLOGY: linear ( i i ) MOLECULE TYPE: genomic DNA ( i v ) ANTI-SENSE: no ( v i ) ORIGINAL SOURCE:
        ( A ) ORGANISM: Pyrococcus Furiosus
        ( C ) INDIVIDUAL ISOLATE:DSM #3638
        ( G ) CELL TYPE: unicellular organism (vii) IMMEDIATE SOURCE:
    (A) LIBRARY:PTO.MBPyroccocus Furiosus Genomic DNA
    (B) CLONE: pEM1

(xi) SEQUENCE DESCRIPTION: SEQ ID NO:2:

```
TTTATGCTTC CGGCTCGTAT GTTGTGTGGA ATTGTGAGCG GATAACAATT TCACACAGGA      60
AACAGCTATG ACCATGATAT CGCCAAGCGC GCAATTAACC CTCACTAAAG GGAACAAAAG    120
CTGGAGCTCC ACCGCGGTGG CGGCCGCTCT AGAACTAGTG GATCTGATGC GTTATCTGGA    180
GCTTGCTCAA CTTTATCAAA AGTTAGAAAA GACAACTATG AAACTTATAA AGACTAGACT    240
TGTCGCCGAC TTCCTGAAAA AAGTACCAGA TGATCATCTG GAGTTCATTC CCTATCTAAT    300
TCTTGGAGAA GTTTTCCAG AGTGGGATGA AAGGGAGCTG GGTGTGGGAG AAAAGCTGTT     360
AATTAAAGCT GTAGCAATGG CCACTGGAAT TGACGCAAAA GAAATCGAAG AGTCTGTAAA    420
AGATACTGGA GACCTTGGAG AGCATAGC CTTAGCTGTA AAGAAAAAGA AGCAGAAGAG      480
CTTCTTCTCT CAGCCCCTCA CAATAAAGAG GGTATATCAA ACCCTTGTAA AGGTTGCAGA    540
AACAACGGGG GAGGGAAGCC AAGATAAAAA AGTAAAGTAT CTAGCTGATT TGTTCATGGA    600
CGCAGAACCT TTAGAAGCTA AGTATCTTGC TCGTACAATC TTAGGAACAA TGAGAACAGG    660
AGTTGCAGAA GGATTGCTTA GAGATGCAAT AGCAATGGCA TTCCACGTAA AGGTAGAGCT    720
TGTTGAGAGA GCTTACATGC TAACGAGTGA TTTCGGATAT GTAGCTAAAA TAGCAAAGCT    780
TGAAGGAAAT GAAGGGCTAG CAAAAGTTCA AGTTCAACTC GGAAAGCCAA TAAAGCCAAT    840
GCTTGCCCAG CAAGCTGCTA GCATAAGAGA TGCACTTCTC GAGATGGGTG GAGAGGCAGA    900
GTTCGAGATT AAATACGATG GAGCAAGGGT GCAGGTGCAC AAGGATGGCT CAAAAATTAT    960
AGTCTATTCT AGAAGACTGG AGAACGTCAC CAGAGCGATT CCAGAAATTG TTGAGGCTCT   1020
AAAAGAGGCA ATAATACCTG AAAAGGCAAT AGTGGAAGGA GAACTTGTGG CAATTGGAGA   1080
AAACGGAAGA CCATTGCCCT TCCAATATGT GCTTAGAAGG TTTAGGAGAA AGCATAACAT   1140
AGAAGAAATG ATGGAAAAGA TACCTCTCGA GCTCAACTTA TTCGACGTTC TCTACGTAGA   1200
TGGACAAAGC TTGATTGACA CTAAGTTCAT TGATAGAAGA AGAACACTTG AAGAAATAAT   1260
AAAGCAGAAT GAAAAGATAA AGGTAGCAGA AAACCTAATA ACAAAGAAAG TCGAGGAAGC   1320
AGAGGCATTT TACAAGAGAG CACTCGAAAT GGGGCACGAG GGATTGATGG CCAAGAGGTT   1380
AGATGCAGTC TACGAACCAG GTAACAGAGG AAAGAAGTGG TTGAAGATAA AGCCCACAAT   1440
GGAGAACTTA GATTTAGTAA TCATAGGAGC AGAATGGGGA GAGGGAAGAA GAGCCCATCT   1500
CTTTGGTTCA TTCATCCTGG GAGCATATGA TCCAGAAACA GGAGAATTCC TAGAGGTAGG   1560
AAAAGTGGGA AGTGGATTCA CAGATGATGA CTTAGTTGAG TTTACGAAGA TGCTAAAGCC   1620
CCTTATTATA AAAGAGGAAG GAAAGAGAGT CTGGCTCCAG CCCAAAGTTG TTATTGAAGT   1680
GACATATCAA GAAATTCAGA AGAGTCCAAA ATACAGAAGT GGATTTGCAT TAAGGTTCCC   1740
AAGGTTCGTT GCACTTAGAG ATGATAAAGG ACCAGAAGAT GCAGATACAA TAGAGAGAAT   1800
CGCACAACTT TACGAGTTGC AAGAAAAGAT GAAAGGAAAA GTGGAAAGCT AAGGTCTAAC   1860
AATAGTCCCG ATACCATTTC CAACTATCGC CATTGAAAGT CTATCCTTGA CTAAACCATT   1920
GATAAGCCAA ACCTCCTCAG TATAATGGAC TAGCTCACTC ACTGCCTCCA ATTTCTTCTT   1980
TATTCCCCCC GTTACATCAA TTCCTGCAGA GCCCTCTAAT TTGTTAGTA GCTCTTTCAA    2040
TTCACTAGCA CTAATTTCTC TAATCAGCTC CCCTCCTGGA AACTTTGTAT ACAATCCATC   2100
AACATCCATA AGAAATATAA CTTTTTCAGG CTTGAAATGC TTAGCTAAAT AGACCATTAT   2160
TTCATCTCCA GAAACTATCT CTATCGTCGA ACCCAATTCG CCCTATAGTG AGTCGTATTA   2220
```

-continued

```
CGCGCGCTCA CTGGCCGTCG TTTTACAACG TCGTGACTGG GAAAACCCTG GCGTTACCCA      2280

ACTTAATCGC CTTGCAGCAC ATCCCCCNNN NNCAGCTGGC TAATAGCGAA GAGGCCCGCA      2340

CCGATCGCCC TTCCCAACAG TTG                                              2363
```

( 2 ) INFORMATION FOR SEQ ID NO:3:

( i ) SEQUENCE CHARACTERISTICS:
        ( A ) LENGTH: 75 bases
        ( B ) TYPE: nucleic acid
        ( C ) STRANDEDNESS: single
        ( D ) TOPOLOGY: linear ( i i ) MOLECULE TYPE: Chemically Synthesized Oligonucleotide ( i i i ) HYPOTHETICAL: no ( i v ) ANTI-SENSE: no ( x i ) SEQUENCE DESCRIPTION: SEQ ID NO:3:

```
ATCGCATGGT CACTCATCGA AGTCGCTCTG TCATAGCCCA TGCTGGACGT ACGACGACTA        60

CTATGTGACT GCACG                                                         75
```

( 2 ) INFORMATION FOR SEQ ID NO:4:

( i ) SEQUENCE CHARACTERISTICS:
        ( A ) LENGTH: 35 bases
        ( B ) TYPE: nucleic acid
        ( C ) STRANDEDNESS: single
        ( D ) TOPOLOGY: linear ( i i ) MOLECULE TYPE: Chemically Synthesized Oligonucleotide ( i i i ) HYPOTHETICAL: no ( i v ) ANTI-SENSE: no ( x i ) SEQUENCE DESCRIPTION: SEQ ID NO:4:

```
GCAGTCACAT AGTAGTCGTC GTACGTCCAG CATGG                                   35
```

( 2 ) INFORMATION FOR SEQ ID NO:5:

( i ) SEQUENCE CHARACTERISTICS:
        ( A ) LENGTH: 35 bases
        ( B ) TYPE: nucleic acid
        ( C ) STRANDEDNESS: single
        ( D ) TOPOLOGY: linear ( i i ) MOLECULE TYPE: Chemically Synthesized Oligonucleotide ( i i i ) HYPOTHETICAL: no ( i v ) ANTI-SENSE: no ( x i ) SEQUENCE DESCRIPTION: SEQ ID NO:5:

```
GCTATGACAG AGCGACTTCG ATGAGTGACC ATGCG                                   35
```

( 2 ) INFORMATION FOR SEQ ID NO:6:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( i i ) MOLECULE TYPE: Chemically Synthesized Oligonucleotide ( i i i ) HYPOTHETICAL: no ( i v ) ANTI-SENSE: no ( x i ) SEQUENCE DESCRIPTION: SEQ ID NO:6:

AGCAACGACT GTTTGCCCGC CAGTT 25

( 2 ) INFORMATION FOR SEQ ID NO:7:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( i i ) MOLECULE TYPE: Chemically Synthesized Oligonucleotide ( i i i ) HYPOTHETICAL: no ( i v ) ANTI-SENSE: no ( x i ) SEQUENCE DESCRIPTION: SEQ ID NO:7:

AACTGGCGGG CAAACAGTCG TTGCT 25

( 2 ) INFORMATION FOR SEQ ID NO:8:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( i i ) MOLECULE TYPE: Chemically Synthesized Oligonucleotide ( i i i ) HYPOTHETICAL: no ( i v ) ANTI-SENSE: no ( x i ) SEQUENCE DESCRIPTION: SEQ ID NO:8:

GTTGTGCCAC GCGGTTGGGA ATGTA 25

( 2 ) INFORMATION FOR SEQ ID NO:9:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( i i ) MOLECULE TYPE: Chemically Synthesized Oligonucleotide ( i i i ) HYPOTHETICAL: no ( i v ) ANTI-SENSE: no ( x i ) SEQUENCE DESCRIPTION: SEQ ID NO:9:

AGCAACGACT GTTTGCCCGC CAGTT 25

( 2 ) INFORMATION FOR SEQ ID NO:10:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: Chemically Synthesized Oligonucleotide ( i i i ) HYPOTHETICAL: no ( i v ) ANTI-SENSE: no ( x i ) SEQUENCE DESCRIPTION: SEQ ID NO:10:

TACATTCCCA ACCGCGTGGC ACCA 24

( 2 ) INFORMATION FOR SEQ ID NO:11:

( i ) SEQUENCE CHARACTERISTICS:
        ( A ) LENGTH: 26 bases
        ( B ) TYPE: nucleic acid
        ( C ) STRANDEDNESS: single
        ( D ) TOPOLOGY: linear ( i i ) MOLECULE TYPE: Chemically Synthesized Oligonucleotide ( i i i ) HYPOTHETICAL: no ( i v ) ANTI-SENSE: no ( x i ) SEQUENCE DESCRIPTION: SEQ ID NO:11:

CAACTGGCGG GCAAACAGTC GTTGCT        26

( 2 ) INFORMATION FOR SEQ ID NO:12:

( i ) SEQUENCE CHARACTERISTICS:
        ( A ) LENGTH: 36 bases
        ( B ) TYPE: nucleic acid
        ( C ) STRANDEDNESS: single
        ( D ) TOPOLOGY: linear ( i i ) MOLECULE TYPE: Chemically Synthesized Oligonucleotide ( i i i ) HYPOTHETICAL: no ( i v ) ANTI-SENSE: no ( x i ) SEQUENCE DESCRIPTION: SEQ ID NO:12:

GACTCCAAGG TTGTGTCCAA TGTGGTCACC TTCGCT        36

( 2 ) INFORMATION FOR SEQ ID NO:13:

( i ) SEQUENCE CHARACTERISTICS:
        ( A ) LENGTH: 36 bases
        ( B ) TYPE: nucleic acid
        ( C ) STRANDEDNESS: single
        ( D ) TOPOLOGY: linear ( i i ) MOLECULE TYPE: Chemically Synthesized Oligonucleotide ( i i i ) HYPOTHETICAL: no ( i v ) ANTI-SENSE: no ( x i ) SEQUENCE DESCRIPTION: SEQ ID NO:13:

AGCGAAGGTG ACCACATTGG ACACAACCTT GGAGTC        36

( 2 ) INFORMATION FOR SEQ ID NO:14:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: Chemically Synthesized Oligonucleotide ( i i i ) HYPOTHETICAL: no ( i v ) ANTI-SENSE: no ( x i ) SEQUENCE DESCRIPTION: SEQ ID NO:14:

GACTCCAAGG TTGTGTCC        18

( 2 ) INFORMATION FOR SEQ ID NO:15:

( i ) SEQUENCE CHARACTERISTICS:

(A) LENGTH: 18 bases
(B) TYPE: nucleic acid
(C) STRANDEDNESS: single
(D) TOPOLOGY: linear ( i i ) MOLECULE TYPE: Chemically Synthesized Oligonucleotide ( i i i ) HYPOTHETICAL: no ( i v ) ANTI-SENSE: no ( x i ) SEQUENCE DESCRIPTION: SEQ ID NO:15:

AATGTGGTCA CCTTCGCT 18

( 2 ) INFORMATION FOR SEQ ID NO:16:

( i ) SEQUENCE CHARACTERISTICS:
(A) LENGTH: 18 bases
(B) TYPE: nucleic acid
(C) STRANDEDNESS: single
(D) TOPOLOGY: linear ( i i ) MOLECULE TYPE: Chemically Synthesized Oligonucleotide ( i i i ) HYPOTHETICAL: no ( i v ) ANTI-SENSE: no ( x i ) SEQUENCE DESCRIPTION: SEQ ID NO:16:

AGCGAAGGTG ACCACATT 18

( 2 ) INFORMATION FOR SEQ ID NO:17:

( i ) SEQUENCE CHARACTERISTICS:
(A) LENGTH: 18 bases
(B) TYPE: nucleic acid
(C) STRANDEDNESS: single
(D) TOPOLOGY: linear ( i i ) MOLECULE TYPE: Chemically Synthesized Oligonucleotide ( i i i ) HYPOTHETICAL: no ( i v ) ANTI-SENSE: no ( x i ) SEQUENCE DESCRIPTION: SEQ ID NO:17:

GGACACAACC TTGGAGTC 18